US010011578B2

(12) United States Patent
Stutzmann et al.

(10) Patent No.: US 10,011,578 B2
(45) Date of Patent: Jul. 3, 2018

(54) COMPOUNDS FOR STABILIZING RYANODINE RECEPTORS FROM ABERRANT LEVELS OF CALCIUM RELEASE

(71) Applicant: Rosalind Franklin University of Medicine and Science, North Chicago, IL (US)

(72) Inventors: Grace E. Stutzmann, Lake Forest, IL (US); Russell Dahl, North Chicago, IL (US); Christopher H. Kaiho, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 15/671,833

(22) Filed: Aug. 8, 2017

(65) Prior Publication Data
US 2018/0022722 A1 Jan. 25, 2018

Related U.S. Application Data

(63) Continuation of application No. 14/716,138, filed on May 19, 2015, now Pat. No. 9,725,429, which is a continuation-in-part of application No. 14/213,614, filed on Mar. 14, 2014, now Pat. No. 9,102,645.

(60) Provisional application No. 61/794,455, filed on Mar. 15, 2013.

(51) Int. Cl.
*C07D 307/52* (2006.01)
*C07D 307/54* (2006.01)
*C07D 405/12* (2006.01)
*C07D 407/12* (2006.01)

(52) U.S. Cl.
CPC ......... *C07D 307/54* (2013.01); *C07D 307/52* (2013.01); *C07D 405/12* (2013.01); *C07D 407/12* (2013.01)

(58) Field of Classification Search
CPC .. C07D 307/52; C07D 307/54; C07D 405/12; C07D 407/12
See application file for complete search history.

(56) References Cited

U.S. PATENT DOCUMENTS

| | | | |
|---|---|---|---|
| 7,915,245 B2 | 3/2011 | Srivastava et al. |
| 8,183,236 B2 | 5/2012 | Neamati et al. |
| 2004/0006124 A1 | 1/2004 | Dong et al. |
| 2009/0088420 A1 | 4/2009 | Neamati et al. |
| 2009/0093531 A1 | 4/2009 | Malkawi |
| 2010/0035932 A1 | 2/2010 | Schepetkin et al. |

FOREIGN PATENT DOCUMENTS

| | | |
|---|---|---|
| CN | 101402620 A | 4/2009 |
| EP | 2708535 A1 | 3/2014 |
| JP | S50-83373 A | 7/1975 |
| JP | 2005-533087 A | 11/2005 |
| JP | 2007024705 A | 2/2007 |
| JP | 2011/500570 A | 1/2011 |
| JP | 2011-518865 A | 6/2011 |
| WO | 2004/004699 A2 | 1/2004 |
| WO | 2004/004699 A3 | 1/2004 |
| WO | 2009/133142 A1 | 11/2009 |
| WO | 2010/151799 A9 | 12/2010 |

OTHER PUBLICATIONS

Bettiol, et al., PLoS Negl Trop Dis, 2009, vol. 3(2), e384.*
Khlebnikov, et al., European Journal of Medicinal Chemistry, 2010, vol. 45(11), pp. 5406-5419.*
Hanna-Elias, A., et al., "Synthesis and Preliminary Screening of Novel Tryptamines as 5-HT4 Receptor Ligands", Current Medical Chemistry, 2010, vol. 17, pp. 2775-2787.
PubChem, Open Chemistry Database, NIH, U.S. National Library of Medicine, National Center for Biotechnology Information, Dec. 5, 2007, pp. 2-14, https://pubchem.ncbi.nlm.nih.gov/compound/. 22088699.
RN: 938019-87-5, Jun. 20, 2007, CN: 4-[5-[[[(5-bromo-s-benzofuranyl)carbonyl]imimo]methyl]-2-furanyl]-3-methyl.
RN: 852695-71-7, Jun. 22, 2005, CN: 4-[5-[[[(4-carboxyphenyl)methyl]imimo]methyl]-2-furanyl]-3-methyl.
RN: 444765-07-5, Aug. 24, 2002, CN: 4-[[[[5-(4-cyanophenyl)-2-furanyl]methylene]amino]methyl].
RN: 444674-11-7, Aug. 22, 2002, CN: Benzenemethanamine, N-[[5-(3-fluorophenyl)-2-furanyl]methylene]-4-methoxy.
RN: 444560-18-3, Aug. 21, 2002, CN: Benzonitrile, 4-[5-[[[(4-methoxyphenyl)methyl]-2-furanyl].
Bettiol, E., et al., "Identification of Three Classes of Heteroaromatic Compounds with Activity against Intracellular Trypanosoma cruzi by Chemical Library Screening", PLoS Negl Trop Dis, 2009, vol. 3(2), e384.
Caffrey, C.R., et al., "Screening of Acyl Hydrazide Proteinase Inhibitors for Antiparasitic Activity against Trypanosoma brucei", International Journal of Antimicrobial Agents, 2002, vol. 19(3), pp. 227-231.
Cimanis, A., et al., "Synthesis and Antibacterial Effect of 2-(2'-furyl)quinoxaline Derivatives", Khimiko-Farmatsevticheskii Zhurnal, 1977, vol. 11(10), pp. 48-53. (Abstract only).
Cui, Z., et al., "New Class of Potent Antitumor Acylhydrazone Derivatives Containing Furan", European Journal of Medicinal Chemistry, 2010, vol. 45(12), pp. 5576-5584.
Farcasan, V., et al., "Derivatives of Furan. XIII. 2-[5'-Formylfuryl(2')]-benzothiazoles", Studia Universitatis Babes-Bolyai, Chemia, 1977, vol. 22(1), pp. 15-18. (Abstract only).

(Continued)

*Primary Examiner* — Valerie Rodriguez-Garcia
(74) *Attorney, Agent, or Firm* — McDonnell Boehnen Hulbert & Berghoff LLP

(57) ABSTRACT

Disclosed herein are methods and compositions comprising compounds capable of normalizing neuronal calcium dys-homeostasis. Also disclosed are methods comprising these compounds for treating neuronal or neurological disorders, including Alzheimer's disease, Parkinson's disease, Huntington's disease, fronto-temporal dementia, Pick's disease, chronic traumatic encepholopathy, traumatic brain injury, stroke, cerebellar ataxia, multiple sclerosis, Down syndrome, and aging-related CNS disorders.

5 Claims, 19 Drawing Sheets

(56) References Cited

OTHER PUBLICATIONS

Frimm, R., et al., "Furan Derivatives. XI. Synthesis and Absorption Spectra of Benzoic Acid [5-(3-nitrophenyl)-2-furfurylidene]- and [5-(4-nitrophenyl)-2-furfurylidene]hydrazides", Chemicke Zvesti, 1968, vol. 22(5), pp. 361-367. (Abstract only).
Frimm, R., et al., "Furan Derivatives. XII. Preparation and Absorption Spectra of [5-(2-nitrophenyl)-2-furfurylidene]benzoylhydrazones", Chemicke Zvesti, 1968, vol. 22(6), pp. 447-451. (Abstract only).
Garcia-Domenech, R., et al., "Application of Molecular Topology to Predict the Inhibition of Trypanosoma cruzi Cruzain by Thiosemicarbazones", Internet Electronic Journal of Molecular Design, 2008, vol. 7(12), pp. 260-272.
Gašparová, R., et al., "Reactions of Substituted Furo[3,2-b]pyrrole-5-carboxhydrazides and their Biological Activity" Central European Journal of Chemistry, 2005, vol. 3(4), pp. 622-646.
Hillers, S., et al., "Tuberculostatic Action of Some 5(-nitrophenyl)furfural Derivatives", Latvijas PSR Zinatnu Akademijas Vestis, 1969, vol. 7, pp. 133-136. (Abstract only).
Jedlovska, E., et al., "Synthesis of 2,5-Disubstituted 1,3,4-Oxadiazoles and their Precursors", Collect. Czech. Chem. Commun., 1994, vol. 59, pp. 1892-1896.
Khlebnikov, A.I., et al., "Computational Structure-Activity Relationship Analysis of Non-Peptide Inducers of Macrophage Tumor Necrosis Favor-x Production", Bioorganic & Medicinal Chemistry, 2008, vol. 16(20), pp. 9302-9312.
Khlebnikov, A., et al., "Computational Structure-Activity Relationship Analysis of Small-Molecule Agonists for Human Formyl Peptide Receptors", European Journal of Medicinal Chemistry, 2010, vol. 45(11), pp. 5406-5419.
Mndzhoyan, A.L., et al., "Furan Derivatives. XXI Some Derivatives of Furan", Doklady Akademii Nauk Armyanskoi SSR, 1958, vol. 27(5), pp. 305-313. (Abstract only).
Paschos, A., et al., "An In Vivo High-Throughput Screening Approach Targeting the Type IV Secretion System Component VirB8 Identified Inhibitors of Brucella abortus 2308 Proliferation", Infection and Immunity, 2011, vol. 79(3), pp. 1033-1043.
Reichstein, T., et al., "Aldehyde Synthesos in the Furan Series. III. Binuclear Furan Substances, Bifuryl and Difurylmethane", Helvetica Chimica Acta, 1932, vol. 15, pp. 1066-1074. (Abstract only).
Smith, M.A., et al., "Identification of the Binding Site of Brucella VirB8 Interaction Inhibitors", Chemistry & Biology, 2012, vol. 19(8), pp. 1041-1048.
Sodha, V., et al., "N-aroylamino-2-(p-carboxyphenyl-fur-2-yl)azomethine", Journal of the Institution of Chemists (India), 2003, vol. 75(4), pp. 119-120. (Abstract only).
Extended European Search Report, received from the European Patent Office, dated Jan. 20, 2017, for European Application No. PCT/US2014/029155, pp. 1-30.
Korchevin, N.A., et al., "Azomethine Derivatives on the Basis of 5-Formyl-2,2'-Bithienyl and 5-Formyl-2,2'-Dithienyl Sulfide", Chemistry of Heterocyclic Compounds, 2003, vol. 39(1), pp. 56-60.
Raghupathi, N., et al., "A One-Pot Selective Synthesis of N-Boc Protected Secondary Amines: Tandem Direct Reductive Amination/N-Boc Protection", Tetrahedron, 2012, vol. 68, pp. 7056-7062.
Supplementary European Search Report, European Patent Office, dated Sep. 16, 2016, pp. 1-8, for European Application No. 14763243.4-1452 based on PCT/US2014/029155.
Inan, S., et al., "The Cytoprotective Effects of Dantrolene: A Ryanodine Receptor Antagonist", Anesthesia & Analgesia, Dec. 2010, vol. 111(6), pp. 1400-1410, doi:10.1213/ANE.0b013e3181f7181c.
Belal, C., et al., "The Homocysteine-Inducible Endoplasmic Reticulum (ER) Stress Protein Herp Counteracts Mutant a-Synuclein-Induced ER Stress via the Homeostatic Regulation of ER-Resident Calcium Release Channel Proteins", Human Molecular Genetics, Nov. 1, 2012, vol. 21(5), pp. 963-977, doi:10.1093/hmg/ddr502.

Braubach, P., et al., "Altered Ca(2+) Signaling in Skeletal Muscle Fibers of the R6/2 Mouse, a Model of Huntington's Disease", Journal of General Physiology, Oct. 27, 2014, vol. 144(5), pp. 393-413, doi:10.1085/jgp.201411255. (Abstract only).
Caporello, E., et al., "The Immunophilin Ligand GPI1046 Protects Neurons from the Lethal Effects of the HIV-1 Proteins GP120 and Tat by Modulating Endoplasmic Reticulum Calcium Load", Journal of Neurochemistry, 2006, vol. 98, pp. 146-155, doi:10.1111/j.1471-46159.2006.03863.x.
Chen, Xi, et al., "Dantrolene is Neuroprotective in Huntington's Disease Transgenic Mouse Model", Molecular Neurodegeneration, 2011, vol. 6(81), pp. 1-12, http://www.molecularneurodegeneration.com/content/6/1/81.
Ferreiro, E., et al., "An Endoplasmic-Reticulum-Specific Apoptotic Pathway is Involved in Prion and Amyloid-Beta Peptides Neurotoxicity", Neurobiology of Disease, May 22, 2006, vol. 23, pp. 669-678.
Ferreiro, E., et al., "The Release of Calcium from the Endoplasmic Reticulum Induced by Amyloid-Beta and Prion Peptides Activates the Mitochondrial Apoptotic Pathway", Neurobiology of Disease, Feb. 20, 2008, vol. 30, pp. 331-342.
Hopp, S., et al., "Differential Neuroprotective and Anti-Inflammatory Effects of L-Type Voltage Dependent Calcium Channel and Ryanodine Receptor Antagonists in the Substantia Nigra and Locus Coeruleus", Journal of Neuroimmune Pharmacology, Oct. 16, 2014, vol. 10(1), pp. 35-44, http://dx.doi.org/10.1007/s11481-014-9568-7. (Abstract only).
Mattson, M., "Calcium and Neurodegeneration", Aging Cell, 2007, vol. 6, pp. 337-350, Doi:10.1111/j.1474-9726.2007.00275.x.
Perry, S.W., et al., "Human Immunodeficiency Virus-1 Tat Activates Calpain Proteases via the Ryandine Receptor to Enhance Surface Dopamine Transporter Levels and Increase Transporter-Specific Uptake on Vmax", The Journal of Neuroscience, Oct. 10, 2010, vol. 30(42), pp. 14153-14164.
Suzuki, M., et al, "Calcium Leak Through Ryanodine Receptor is Involved in Neuronal Death Induces by Mutant Huntingtin", Biochemical and Biophysical Research Communications, 2012, vol. 429, pp. 18-23.
Thibault, O., et al., "Expansion of the Calcium Hypothesis of Brain Aging and Alzheimer's Disease: Minding the Store", Aging Cell, 2007, vol. 6, pp. 307-317, Doi:10.1111/j.1474-9726.2007.00295.
Davis, C.S., et al., "Synthesis of 5-Phenyl-2-furaldehyde", Chemistry Division, The Norwich Pharmacal Company, Mar. 1967, vol. 4, pp. 153-154.
De Oliveira, R.B., et al., "Synthesis, Biological Evaluation and Molecular Modeling of Arylfurans as Potential Trypanothione Reductase Inhibitors", Quim. Nova, 2008, vol. 31(2), pp. 261-267.
Yarrow, J.C., et al., "Phenotypic Screening of Small Molecule Libraries by High Throughput Cell Imaging", Combinatorial Chemistry & High Throughput Screening, Jun. 1, 2003, vol. 6(4), pp. 279-286.
RN: 852695-71-7, Jun. 22, 2005, CN: 4-[5-[[[(4-carboxyphenyl)methyl]imino]methyl]-2-furanyl]-3-methyl-benzoic acid.
RN: 444765-07-5, Aug. 24, 2002, CN: 4-[[[[5-(4-cyanopheny1)-2-furanyl]methylene]amino]methyl]-benzoic acid.
RN: 444674-11-7, Aug. 22, 2002, CN: N-[[5-(3-fluorophenyl)-2-furanyl]methylene]-4-methoxy-benzenemethanamine.
RN: 444560-18-3, Aug. 21, 2002, CN: 4-[5-[[[(4-methoxyphenyl)methyl]imino]methyl]-2-furanyl]-benzonitrile.
Antonell A., et al., "A Preliminary Study of the Whole-Genome Expression Profile of Sporadic and Monogenic Early-Onset Alzheimer's Disease", Neurobiology of Aging, vol. 34, pp. 1772-1778, Jan. 28, 2013.
Berge, S. M., et al., "Pharmaceutical Salts", Journal of Pharmaceutical Sciences, vol. 66, pp. 1-19, Jan. 1977. (Abstract only).
Briggs, C. A., et al., "Beta Amyloid Peptide Plaques Fail to Alter Evoked Neuronal Calcium Signals in APP/PS1 Alzheimer's Disease Mice", Neurobiology of Aging, vol. 34, pp. 1632-1643, Jan. 18, 2013.
Bruno, A. M., et al., "Altered Ryanodine Receptor Expression in Mild Cognitive Impairment and Alzheimer's Disease", Neurobiology of Aging, vol. 33, pp. 1001.e1-1001.e6, 2012.

(56) References Cited

OTHER PUBLICATIONS

Chakroborty, S., et al., "Stabilizing ER Ca2+ Channel Function as an Early Preventative Strategy for Alzheimer's Disease", PLOS ONE, vol. 7(12), e52056, doi:10.1371/journal.pone.0052056, Dec. 21, 2012.

Chakroborty, S., et al., "Calcium Channelopathies and Alzheimer's Disease: Insight into Therapeutic Success and Failures", European Journal of Pharmacology, pii:S0014-2999(13)00883-2, doi:10.1016/j.ejphar.2013.11.012 [Epub ahead of print], Dec. 6, 2013.

Chakroborty, S., et al, "Deviant Ryanodine Receptor-Mediated Calcium Release Resets Synaptic Homeostasis in Presymptomatic 3xTg-AD Mice", The Journal of Neuroscience, vol. 29(30), pp. 9458-9470, Jul. 29, 2009.

Galeotti, N., et al., "Different Involvement to Type 1, 2, and 3 Ryanodine Receptors in Memory Process", Learning and Memory, vol. 15, pp. 315-323, 2008.

Golde, T. E., et al., "Avoiding Unintended Toxicity", Science, vol. 324, pp. 603-604, 2009.

Goussakov, I., et al., "NMDA-Mediated Ca2+ Influx Drives Aberrant Ryanodine Receptor Activation in Dendrites of Young Alzheimer's Disease Mice", The Journal of Neuroscience, vol. 30(36), pp. 12128-12137, Sep. 8, 2010.

Kelliher, M., et al., "Alterations in the Ryanodine Receptor Calcium Release Channel Correlate with Alzheimer's Disease Neurofibrillary and β-Amyloid Pathologies", Neuroscience, vol. 92(2), pp. 499-513, 1999.

Kerchner, G. A., et al., "Bapineuzumab", Expert Opinion on Biological Therapy, vol. 10(7), pp. 1121-1130, doi:10.1517/14712598.2010.493872, Jul. 2010.

Liu, X., et al., "Role of Leaky Neuronal Ryanodine Receptors in Stress-Induced Cognitive Dysfunction", Cell, vol. 150, pp. 1055-1067, Aug. 31, 2012.

Oules, B., et. al, "Ryanodine Receptor Blockade Reduces Amyloid-β Load and Memory Impairments in Tg2576 Mouse Model of Alzheimer Disease", The Journal of Neuroscience, vol. 32(34), pp. 11820-11834, Aug. 22, 2012.

Querfurth, H. W., et al., Caffeine Stimulates Amyloid β-Peptide Release from β-Amyloid Precursor Protein-Transfected HEK293 Cells, Journal of Neurochemistry, vol. 69, pp. 1580-1591, 1997.

Peng, J., et al., "Dantrolene Ameliorates Cognitive Decline and Neuropathology in Alzheimer Triple Transgenic Mice", Neuroscience Letters, 2012, http://dx.doi.org/10.1016/j.neulet.2012.04.008.

Supnet, C., et al., "Amyloid-β-(1-42) Increases Ryanodine Receptor-3 Expression and Function in Neurons of TgCRND8 Mice", The Journal of Biological Chemistry, vol. 281(50), pp. 38440-38447, Oct. 18, 2006.

Sutton, R. L., et al, "Unilateral Cortical Contusion Injury in the Rat: Vascular Disruption and Temporal Development of Cortical Necrosis", Journal of Neurotrauma, vol. 10(2), pp. 135-149, Mar. 26, 2009. (Abstract only).

Zhang, H., et al., "Role of Presenilins in Neuronal Calcium Homeostasis", The Journal of Neuroscience, vol. 30(25), pp. 8566-8580, Jun. 23, 2010.

Hosoya, T., et al., "Dantrolene Analogues Revisited: General Synthesis and Specific Functions Capable of Discriminating two Kinds of Ca2+ Release from Sarcoplasmic Reticulum of Mouse Skeletal Muscle", Bioorg Med Chem, Mar. 6, 2003, vol. 11(5), pp. 663-673. Pubchem CID 22088699, [<URL:http://pubchem.ncbi.nlm.nih.gov/summary/summary.cgi?cid=22088699>].

\* cited by examiner

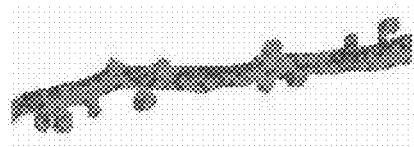
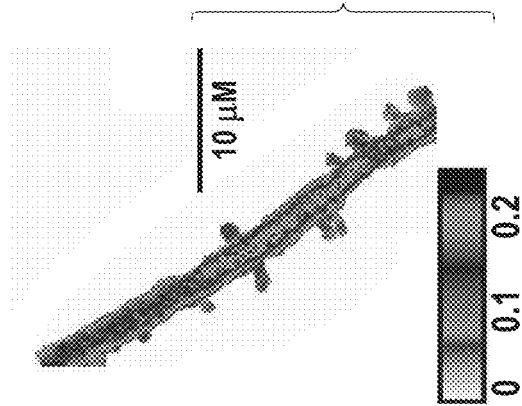
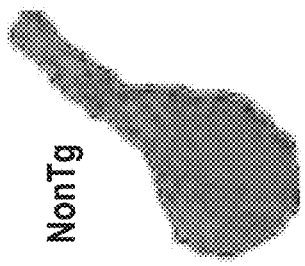
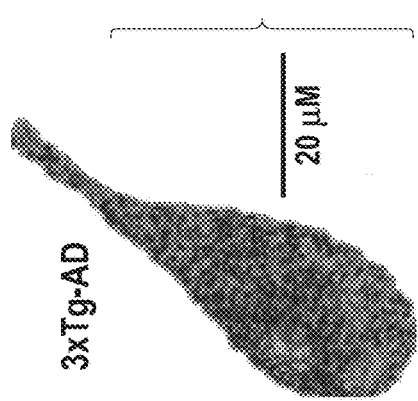

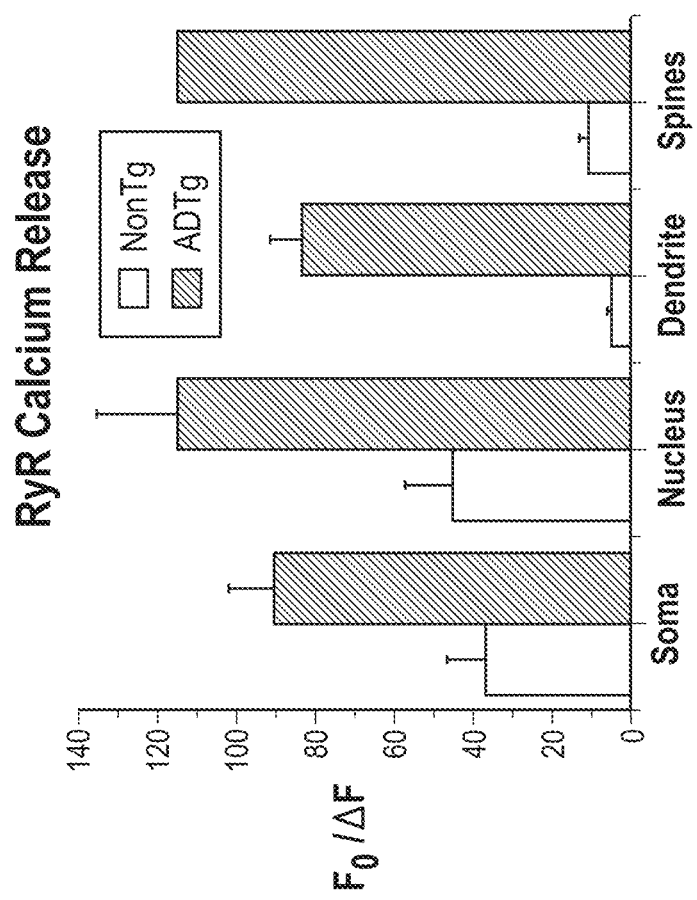

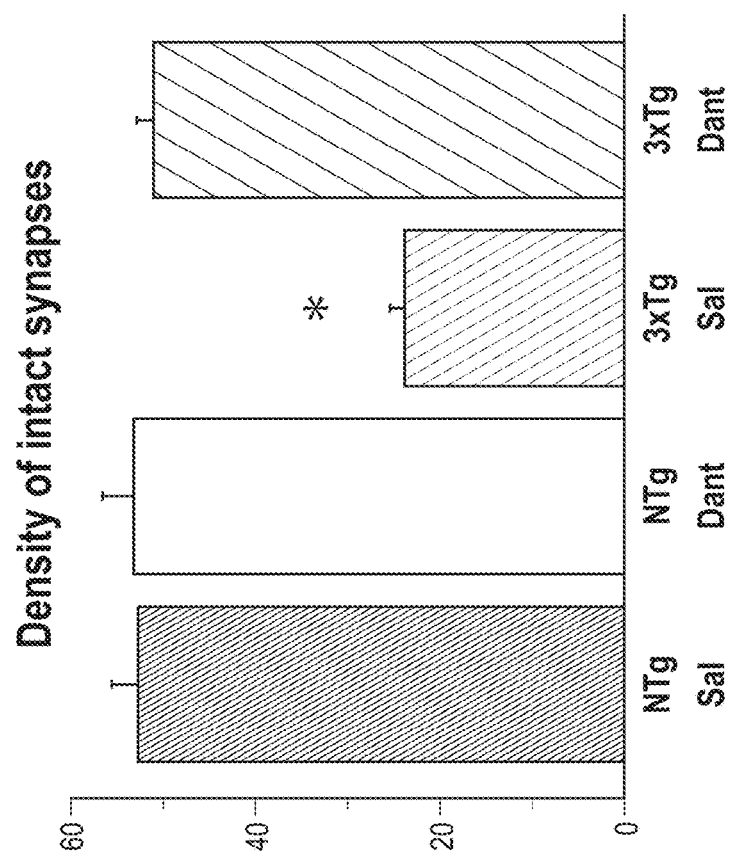

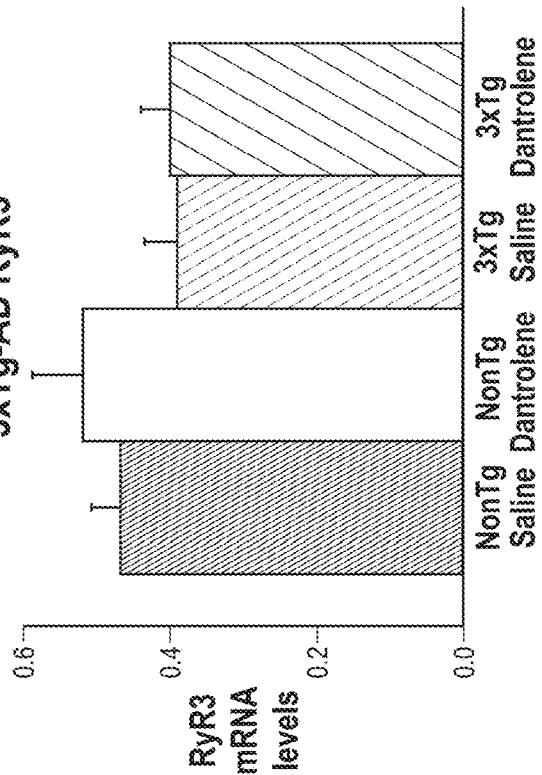
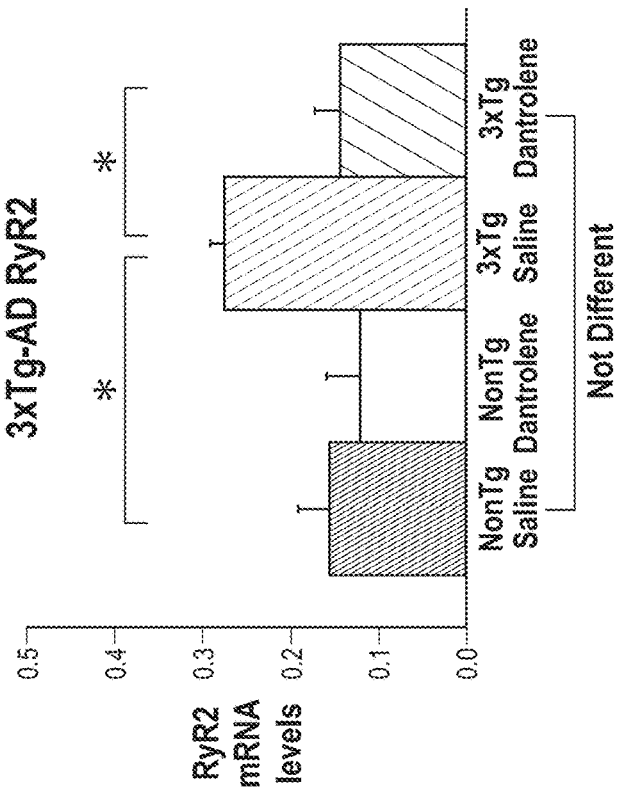

Dentate gyrus pTau staining
TgCRND8 Dantrolene Treated

Dentate gyrus pTau staining
TgCRND8 Saline Treated

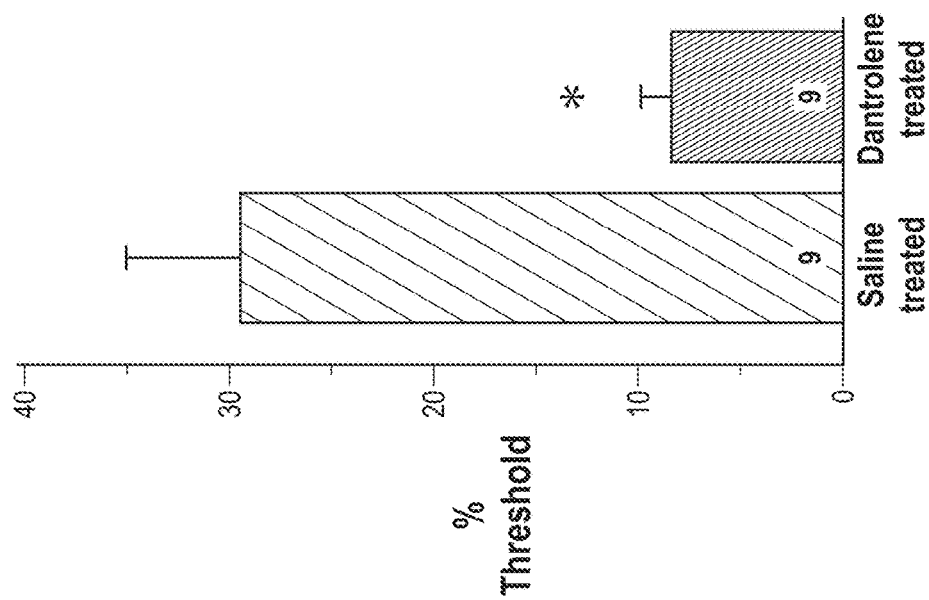

Traumatic Brain injury: Dentate gyrus pTau staining

TgCRND8 Dantrolene Treated

Traumatic Brain injury: Dentate gyrus pTau staining

TgCRND8 Saline Treated

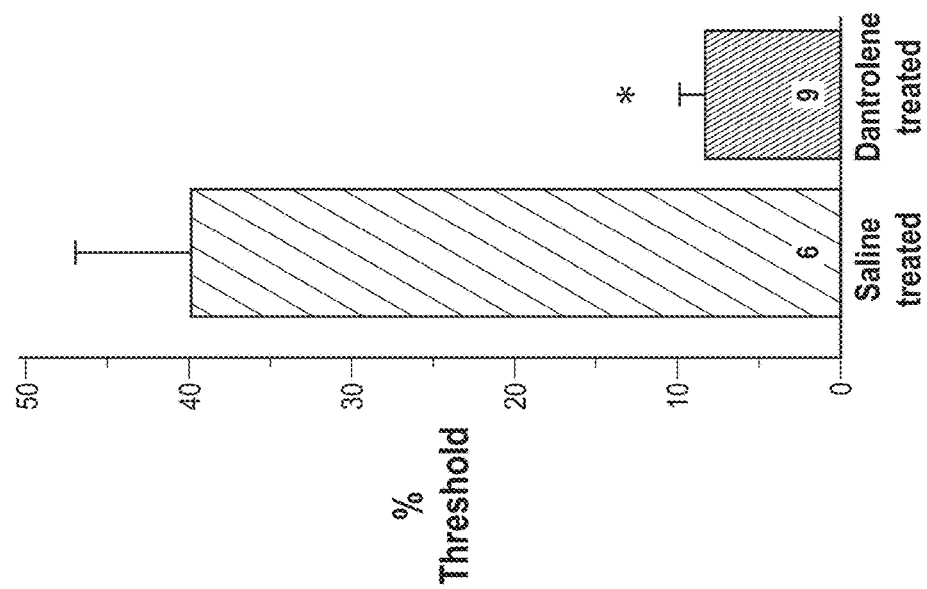

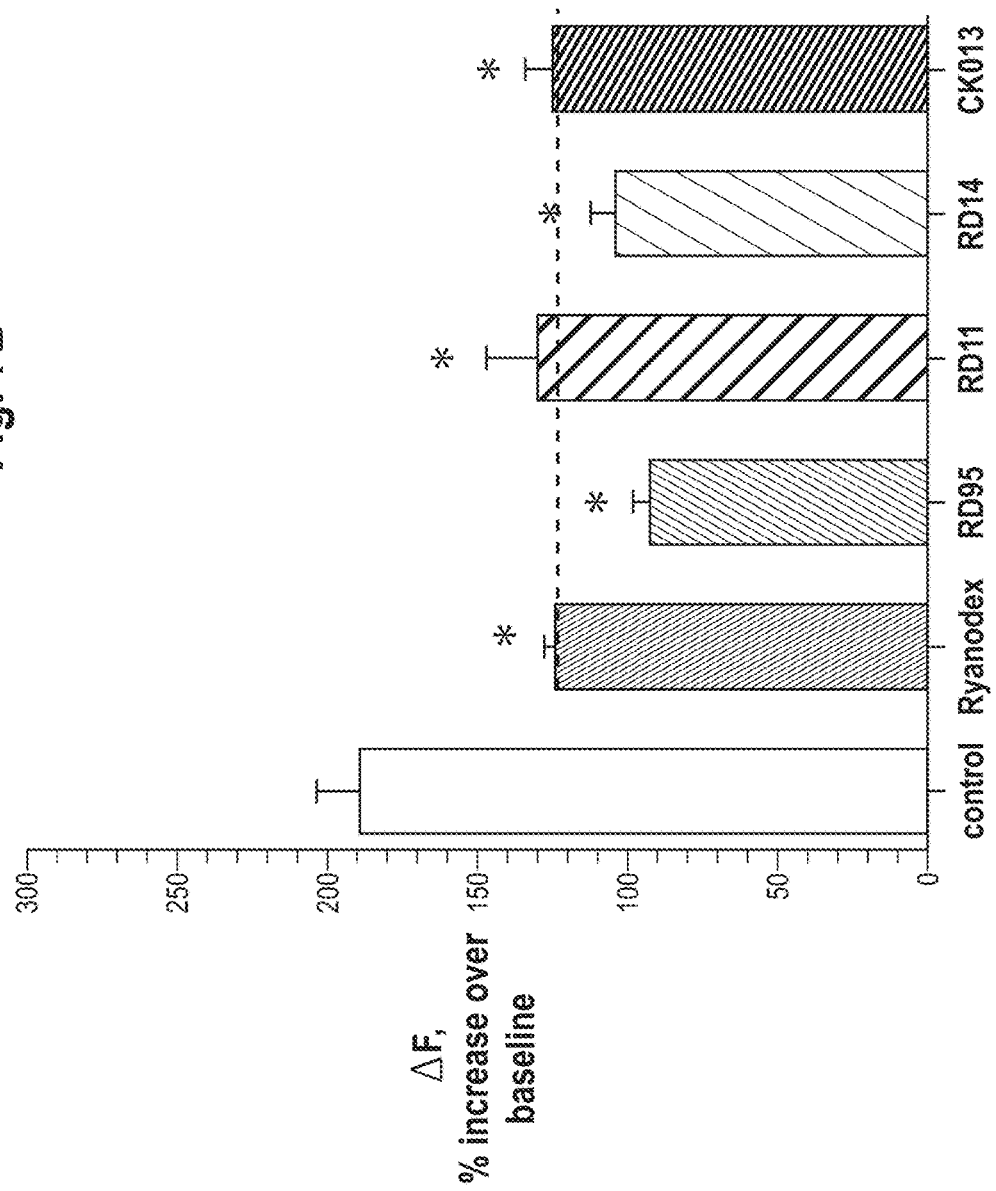

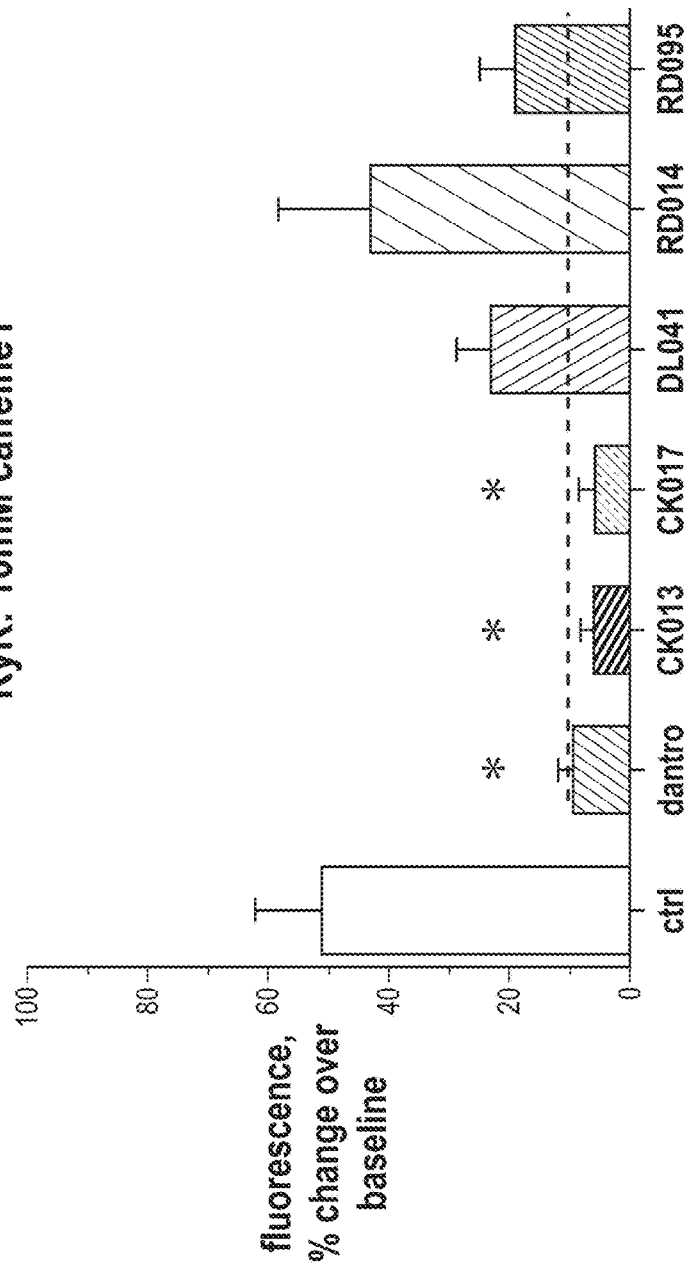

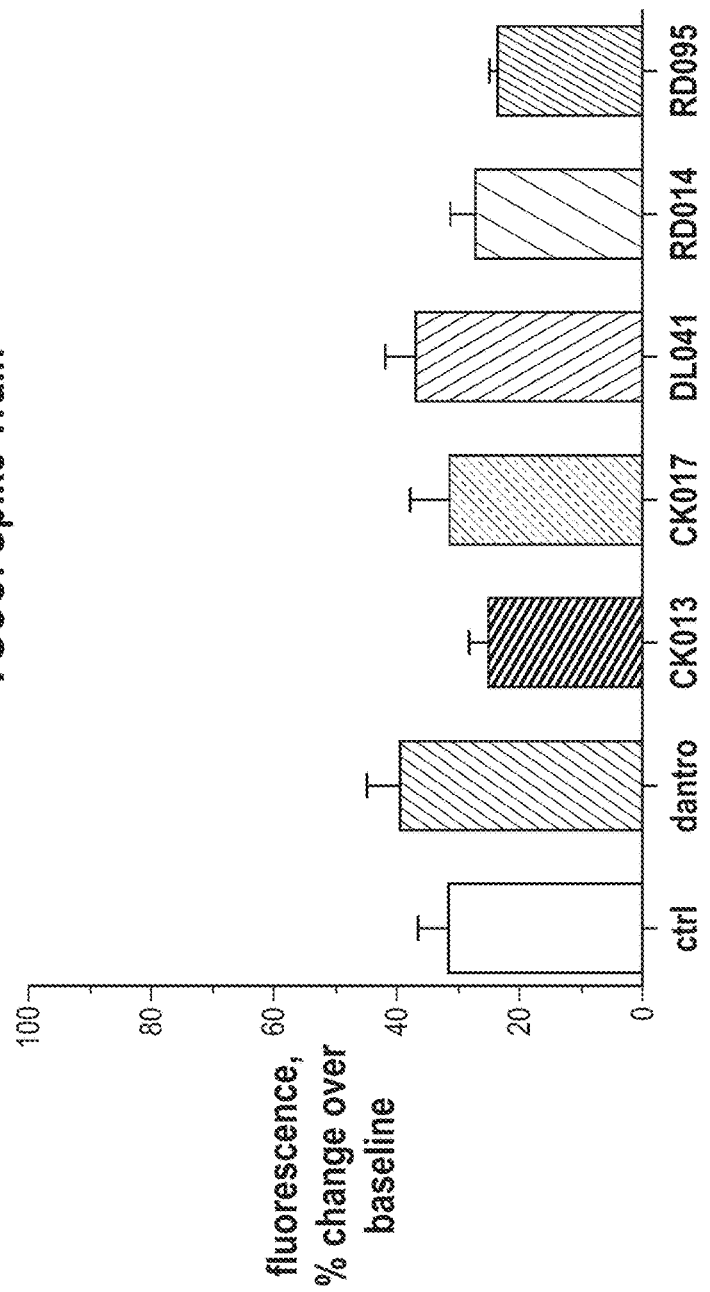

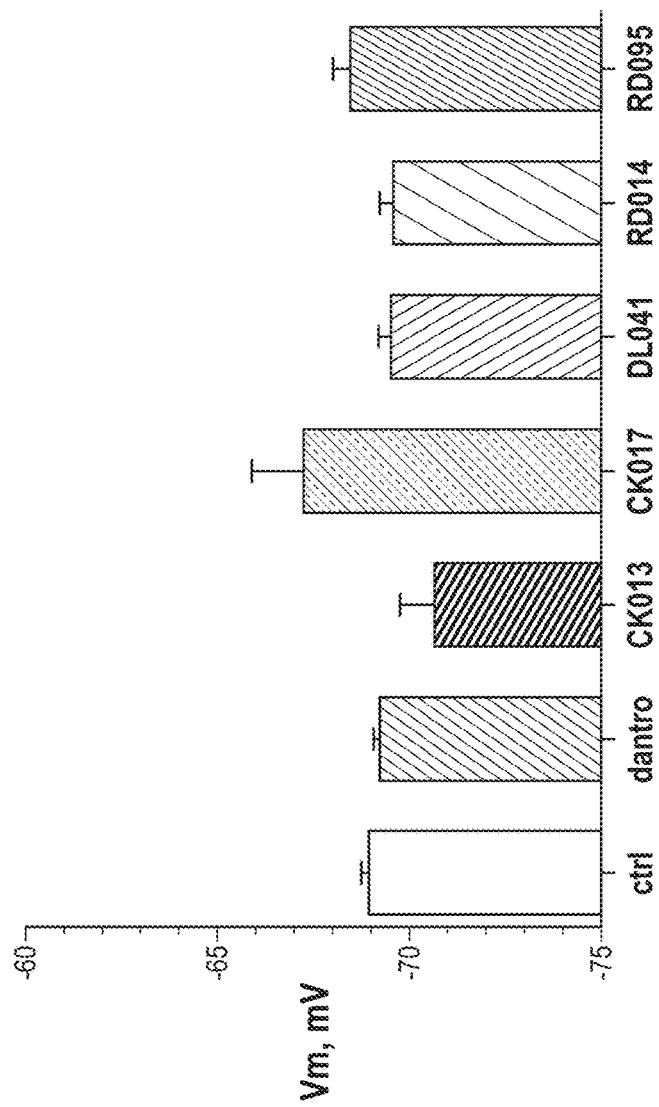

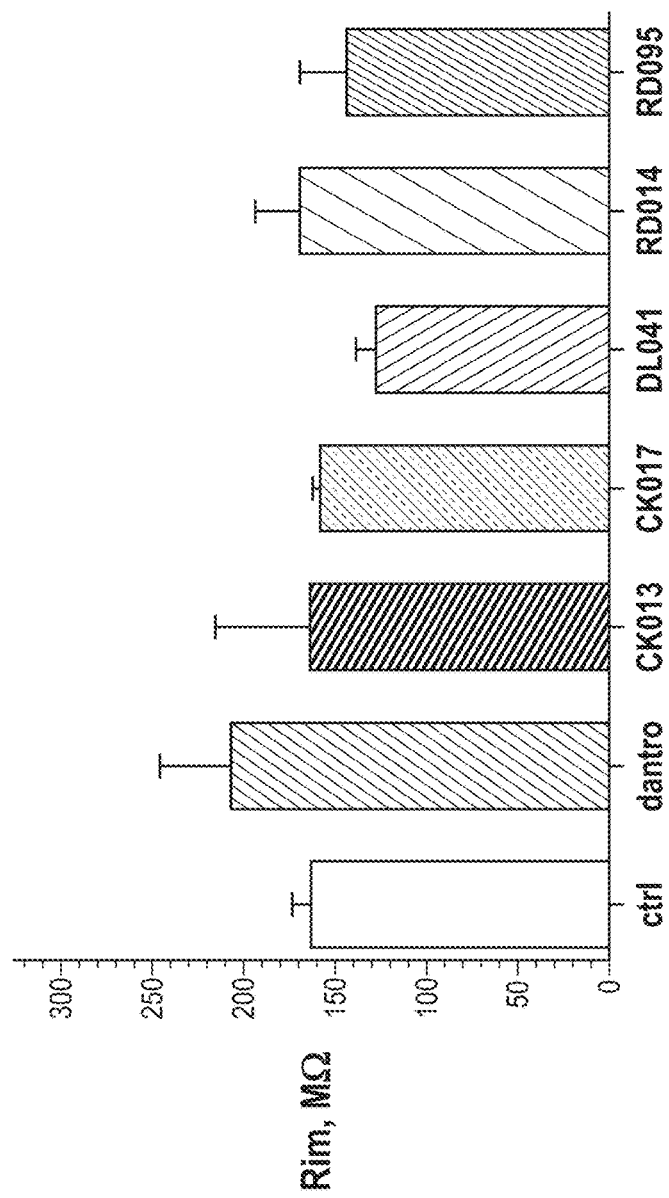

FIGURE 10
Table 1. Structure-activity relationships for compounds selected from the initial round of synthesis.
| | $R_1$ | $R_2$ | $R_3$ | $R_4$ | $R_5$ | MW | LogP | $Ca^{2+}$ inc | Brain / Plasma | $Ca^{2+}$ trace |
|---|---|---|---|---|---|---|---|---|---|---|
| Caffeine (+ con) | -- | -- | -- | -- | -- | -- | -- | 3.09 | -- |  |
| dantrolene | H | H | $NO_2$ | H |  | 314 | 1.7 | 1.96 | <0.01 |  |
| RD05 | H | H | H | H |  | 269 | 1.8 | 1.43 | 0.5 |  |
| RD09 | H | $NO_2$ | H | H |  | 273 | 2.5 | 1.06 | nd |  |
| RD10 | Cl | H | $NO_2$ | H |  | 349 | 3.4 | 4.25 | nd |  |
| RD11 | H | $NO_2$ | H | H |  | 336 | 3.0 | 1.38 | nd |  |
| RD14 | $CH_3$ | $CH_3$ | $NO_2$ | H |  | 302 | 3.2 | 2.38 | 1.6 |  |
| RD54 | Cl | H | $NO_2$ | H |  | 385 | 5.1 | >6 | nd |  |
| RD77 | H | H | Br | H |  | 414 | 5.0 | >6 | nd |  |
| RD83 | H | H | $NO_2$ | H |  | 404 | 5.5 | >6 | nd |  |
| RD91 | Cl | Cl | H | H |  | 360 | 4.4 | >6 | nd |  |
| RD95 | $OCH_3$ | H | H | $NO_2$ |  | 304 | 2.5 | 2.11 | nd |  |

COMPOUNDS FOR STABILIZING RYANODINE RECEPTORS FROM ABERRANT LEVELS OF CALCIUM RELEASE

CROSS-REFERENCE TO RELATED APPLICATIONS

This application is a continuation of U.S. patent application Ser. No. 14/716,138, filed May 19, 2015, now U.S. Pat. No. 9,725,429, which is a continuation-in-part of U.S. patent application Ser. No. 14/213,614, filed Mar. 14, 2014, now U.S. Pat. No. 9,102,645, which claims the benefit of priority from U.S. Provisional Application No. 61/794,455, filed Mar. 15, 2013, which are incorporated by reference herein in its entirety.

BACKGROUND

An effective drug regimen remains elusive for the treatment of neurodegenerative diseases including Alzheimer's disease (AD), Parkinson's disease, Huntington's disease, fronto-temporal dementia, as well as brain injury, such as traumatic brain injury (TBI) and related cognitive deficits, and CTE (chronic traumatic encephalopathy).

To date, multiple Phase III clinical trials for the treatment of AD and other neurodegenerative diseases have been unsuccessful, not necessarily because they did not engage their target, but the target may be dissociated from the desired therapeutic outcome, namely retention of cognitive abilities. The majority of the clinical trials for AD therapies have focused on amyloid precursor protein (APP) processing, and while amyloid levels were reduced in many of the clinical trials, there was no positive effect on memory performance. Furthermore, complications such as toxicity problems and worsened cognitive functions have emerged (Golde et al., 2009, *Science* 324:603-604; Kerchner & Boxer, 2010, *Expert Opinion on Biological Therapy* 10:1121-1130; Chakroborty and Stutzmann, 2013 Dec. 6, *Eur J Pharmacol.*, pii: S0014-2999(13)00883-2. doi: 10.1016/j.ejphar.2013.11.012 [Epub ahead of print]). A possible reason why these compounds did not succeed is that they were administered too late after the cellular and synaptic pathology occurred, and clearing amyloid at this stage would not improve synaptic damage.

An alternative approach to treatment of AD and other neurodegenerative diseases is to target aberrant pathogenic calcium signaling cascades. Stabilization of calcium signaling targets a pathogenic mechanism that is tied to many major features and risk factors of neurodegenerative diseases. Rather than targeting a single diagnostic endpoint, such as amyloid aggregation, this strategy aims to normalize a pathogenic accelerant—namely, sustained calcium dyshomeostasis—that is linked to amyloid pathology, tau hyperphosphorylation, apoptosis, synaptic pathophysiology, and memory deficits.

Calcium signaling in neurons is fundamental to numerous critical functions, including gene transcription, cell death, synaptic integrity, synaptic plasticity, and memory encoding. For example, early increases in endoplasmic reticulum (ER) calcium release through ryanodine receptor (RyR) channels occur in a host of AD models, and in cells from familial and sporadic AD patients. Notably, RyR isoform 2 (RyR2) expression is altered in AD patients and mouse models as well. Neuronal calcium dyshomeostasis is linked to all the major risk factors, histopathological features, synaptic deficits, and cognitive impairments that define AD; therefore, stabilizing ER calcium can broadly impact a range of AD-linked pathologies. Several recent studies have demonstrated that treating neurons from AD mice with dantrolene, a clinically available RyR stabilizer, reduces amyloid deposition, improves memory performance, reverses intracellular calcium alterations, and normalizes RyR expression (Chakroborty and Stutzmann, 2013 Dec. 6, *Eur J Pharmacol.*, pii: S0014-2999(13)00883-2. doi: 10.1016/j.ejphar.2013.11.012 [Epub ahead of print]; Oules et al., 2012, *Journal of Neuroscience* 32:11820-11834). Similar therapeutic effects are also evident with models of traumatic brain injury (TBI). Chronic dantrolene treatment in TgCRND8 mice after exposure to a mild TBI markedly reduces the amount of pathological tau phosphorylation (FIG. 5). However, dantrolene may be pathogenic; chronic oral treatment (10+ months) with dantrolene was found to increase amyloid pathology (Zhang et al., 2010, *Journal of Neuroscience* 30:8566-8580).

Thus, there is a need in the art for novel compounds capable of stabilizing ryanodine receptor channels.

SUMMARY

The present disclosure provides certain advantages and advancements over the prior art. In particular, the present disclosure provides compositions and methods comprising novel RyR-targeted small molecule compounds. Treatment with the RyR channel stabilizers disclosed herein normalizes aberrant ER calcium signaling and preserves synaptic functions toward treating neurodegenerative diseases, such as Alzheimer's disease, where RyR channel stabilizers reduce amyloid pathology.

Thus, one aspect the disclosure provides compounds of formula I:

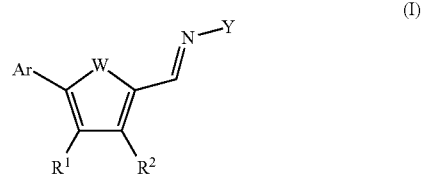

(I)

or a pharmaceutically acceptable salt thereof, wherein
Ar is aryl or heteroaryl, each of which is optionally substituted with 1, 2, 3, 4, or 5 $R^6$ groups;
W is S or O;
Y is substituted (aryl)$C_{1-6}$ alkyl- or

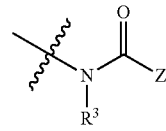

where
Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups;
$R^3$ is hydrogen, or $R^3$ together with Z optionally forms a heterocyclic ring optionally substituted with one or more of $R^7$ groups;
$R^1$ and $R^2$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$- alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino;

$R^4$ and $R^5$ are each independently selected from hydrogen, $C_{1-6}$ alkyl, $C_{1-6}$ haloalkyl, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and (aryl)-heteroaryl-CH=N—, or $R^4$ and $R^5$ together with nitrogen to which they are attached forms a heterocyclic ring, wherein each moiety is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino; and $R^6$ and $R^7$ are each independently selected from halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and oxo, wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino;

provided that the compound is not 1-{[5-(4-nitrophenyl)-2-furyl]methylideneamino}imidazolidine-2,4-dione or 1-{[5-(4-bromophenyl)-2-furyl]methylideneamino}imidazolidine-2,4-dione.

In some embodiments, Ar is aryl optionally substituted with 1, 2, 3, 4, or 5 $R^6$ groups.

In some embodiments, the disclosure provides compounds of formula I where the compound is of formula II:

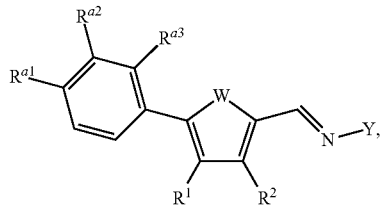

(II)

wherein $R^{a1}$, $R^{a2}$, and $R^{a3}$ are independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, and di($C_{1-4}$ alkyl)carbamyl.

In some embodiments, W is O. In some embodiments, $R^1$ and $R^2$ are both hydrogen. In some embodiments, the disclosure provides compounds of formula I or II wherein Y is

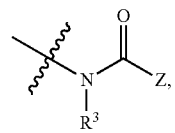

where Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups; and $R^3$ is hydrogen.

In some embodiments, Z is methyl or ethyl. In some embodiments, Z is benzyl. In some embodiments, Z is pyridinyl. In some embodiments, Z is $NR^4R^5$. In some embodiments, $R^4$ and $R^5$ are hydrogen. In some embodiments, $R^4$ and $R^5$ together with nitrogen form piperazinyl ring optionally substituted with $C_{1-3}$ alkyl, $C_{1-3}$ alkoxy, amino, $C_{1-3}$ alkylamino, and di-$C_{1-3}$-alkylamino In some embodiments, the disclosure provides compounds of formula I or II wherein Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups; and $R^3$ together with Z optionally forms a heterocyclic ring optionally substituted with one or more of $R^7$ groups.

In some embodiments, the disclosure provides compounds of formula I, wherein the compounds are selected from the group consisting of:

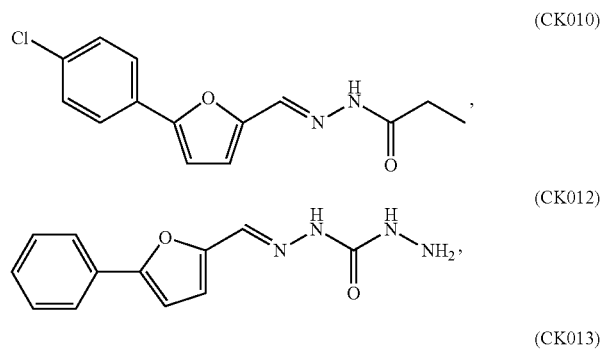

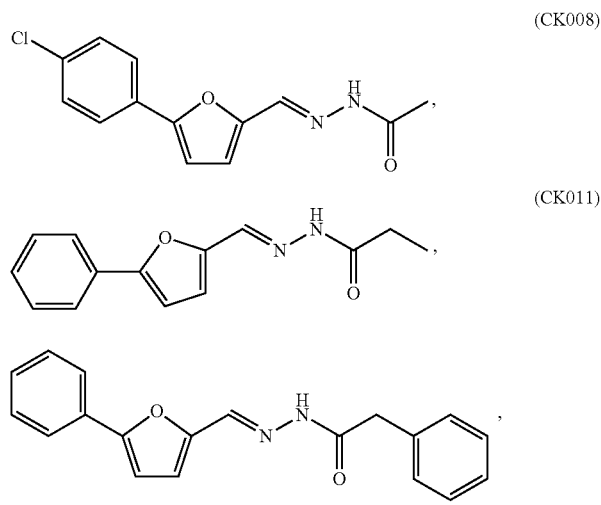

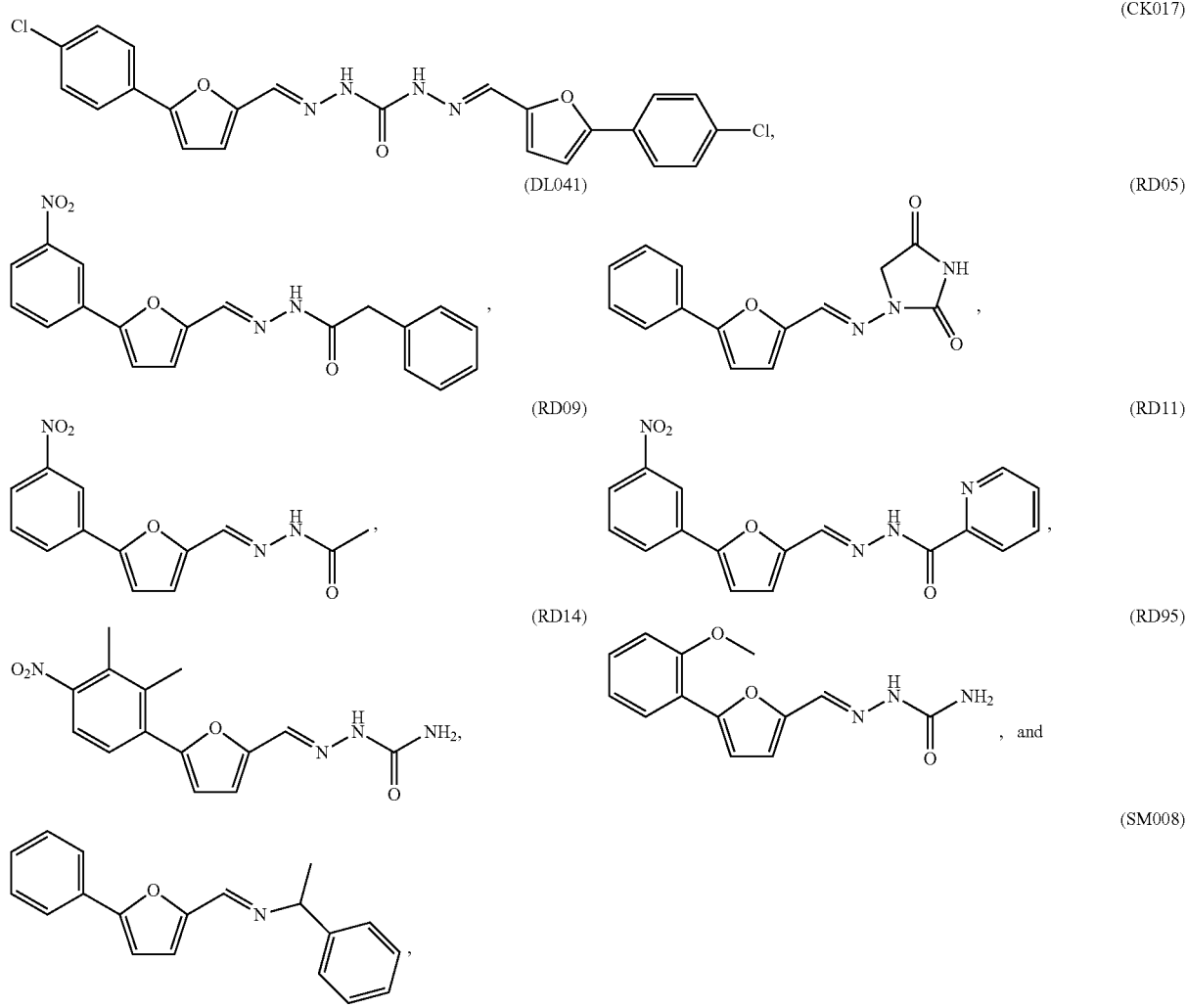

or a pharmaceutically acceptable salt thereof.

The disclosure also provides synthetic intermediates that are useful in making the compounds of formula I or II. The disclosure also provides methods of preparing compounds of the disclosure and the intermediates used in those methods.

Another aspect of the disclosure provides for pharmaceutical composition comprising a pharmaceutically acceptable carrier, solvent, adjuvant or diluent and one or more compounds of formula I or II.

In another aspect, the disclosure provides methods for normalizing neuronal calcium dyshomeostasis in a subject comprising administering to the subject an effective amount of one or more compounds of formula I or II. In some embodiments, the subject is a human subject.

In another aspect, the disclosure provides methods for treating a neurological or neurodegenerative disorder in a subject comprising administering to the subject an effective amount of one or more compounds of formula I or II.

In another aspect, the disclosure provides compositions for treating a neurological or neurodegenerative disorder comprising one or more compounds of formula I or II.

In another aspect, the disclosure provides uses of one or more compounds of formula I or II for preparing compositions for treating a neurological or neurodegenerative disorder.

In some embodiments, the neurological or neurodegenerative disorder is Alzheimer's disease, Parkinson's disease, Huntington's disease, fronto-temporal dementia, Pick's disease, chronic traumatic encepholopathy, traumatic brain injury, stroke, cerebellar ataxia, multiple sclerosis, Down syndrome, or an aging-related CNS disorder. In some embodiments, the neurological or neurodegenerative disorder is Alzheimer's disease. In some embodiments, the subject is a human subject.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, in which:

FIG. 1 shows representative images of RyR-evoked $Ca^{2+}$ responses within the soma (FIG. 1A) or dendrites (FIG. 1B)

from a NonTg hippocampal CA1 neuron. FIGS. 1C and 1D illustrate the same as above except in an AD neuron. These results demonstrate increased RyR-evoked $Ca^{2+}$ release in 3×Tg-AD neurons. FIG. 1E is a bar graph that shows RyR-evoked $Ca^{2+}$ responses averaged per compartment for NonTg light gray and AD dark gray neurons. In all compartments, the AD values are significantly greater than NonTg; p<0.05.

FIG. 3 shows normalization of RyR2 expression levels in AD transgenic mice after 4 weeks of dantrolene treatment. Bar graphs show relative mRNA expression levels of the RyR2 (FIG. 3A) and RyR3 (FIG. 3B) isoforms from the hippocampus of NonTg and AD-Tg mice (3×Tg-AD, shown; APP/PS1, not shown) treated with 0.9% saline or 10 mg/kg dantrolene. AD-Tg mice treated with dantrolene show normalized expression levels of RyR2 compared to saline treated AD-Tg mice. *=p<0.05;

FIGS. 7A and 7B are histograms showing maximal calcium responses in cultured N2A cells upon strong stimulation with the RyR agonist, caffeine (10 mM). In FIG. 7A, the average maximal RyR-evoked calcium response is shown with the solid light gray bar, the darker gray bar to its right shows the reduced calcium response to the same agonist in cells pre-incubated with the RyR channel stabilizer dantrolene (Ryanodex, 10 mM) for 30 minutes. Here, the evoked RyR-calcium response is reduced by over 60%. The following (patterned) bars show cells incubated in various RyR channel stabilizers disclosed herein (10 μM), and the majority of these show similar to enhanced calcium stabilizing properties (dotted line represents the desired range of effects) compared to dantrolene. FIG. 7B demonstrates the same series of experiments conducted with additional sets of compounds. N=3-6 plates per compound; * p<0.05, one-way ANOVA.

FIG. 8 shows the effects of novel RyR-stabilizing compounds on neuronal calcium signaling and electrophysiological membrane properties in 3×Tg-AD mouse models. Hippocampal brain slices were exposed to the RyR agonist, caffeine, under control (ctrl) conditions or after incubation in dantrolene or one of the RyR channel stabilizing compounds disclosed herein (10 μM, 1 hour). RyR-evoked calcium responses (FIG. 8A) and voltage-gated calcium responses (FIG. 8B) were subsequently measured in CA1 pyramidal neurons with 2-photon microscopy and whole cell patch clamp recordings. Resting membrane potential (RMP; FIG. 8C) and membrane input resistance (Ri; FIG. 8D) were also measured under these conditions. In FIG. 8A, the enhanced RyR-evoked calcium response in the AD neurons under control conditions were significantly reduced to within physiological levels with dantrolene, CK013, and CK017. Dashed line indicates approximate desired level of the RyR-evoked calcium response. There were no significant differences in the voltage-gated calcium responses (FIG. 8B), RMP (FIG. 8C), or Ri (FIG. 8D) upon incubation with the various compounds. *p<0.05. n=4-7 neurons/group.

FIG. 10 illustrates complete Table 1, which provides structure-activity relationships for compounds selected from the initial round of synthesis.

Figure 2A:
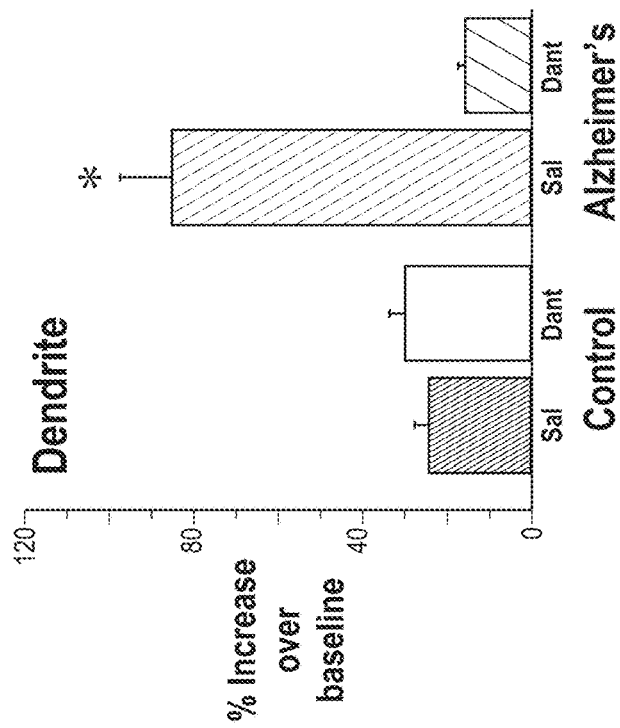
FIG. 2 shows reversal of AD pathology in AD mouse models after 4-week treatment with dantrolene. Saline (Sal)-treated APP/PS1 mice have significantly increased ER calcium responses in the soma (FIG. 2A) and dendrites (FIG. 2B), whereas 4-week dantrolene treatment normalizes this calcium response, with no effect on the NonTg controls. Representative grayscale 2-photon images are shown in FIG. 2C.
As shown in FIG. 2D, beta amyloid levels, indicated by 4G8 immunostaining, are reduced by 45% in hippocampus and cortex of dantrolene-treated mice.
FIG. 2E demonstrates that synaptic integrity, measured by colocalization of pre- and post-synaptic markers (synaptophysin and PSD-95 immunostaining, respectively) with confocal microscopy, is restored in the dantrolene-treated AD mice. *=p<0.05
Figure 2B:
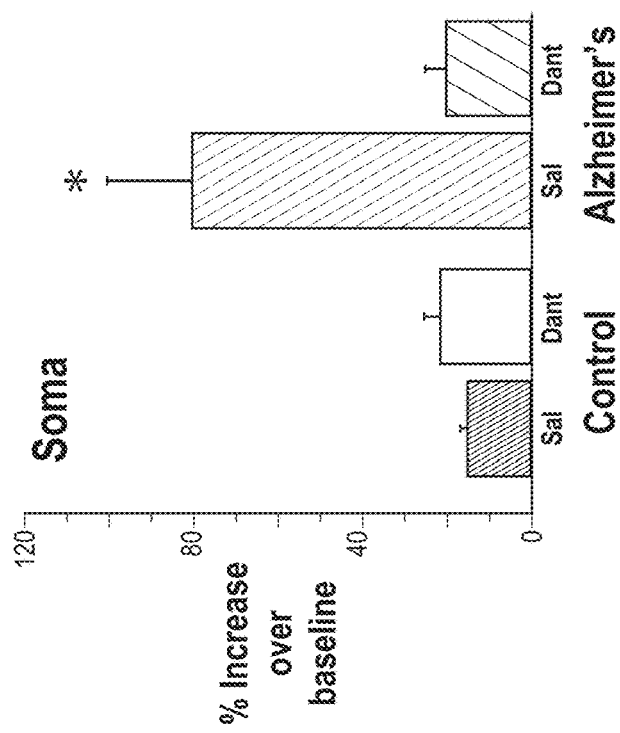
Figure 2C:
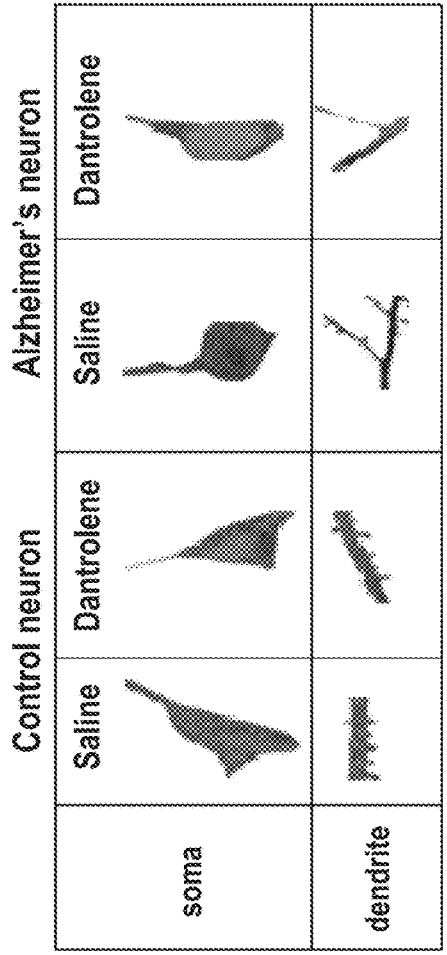
Figure 2D:
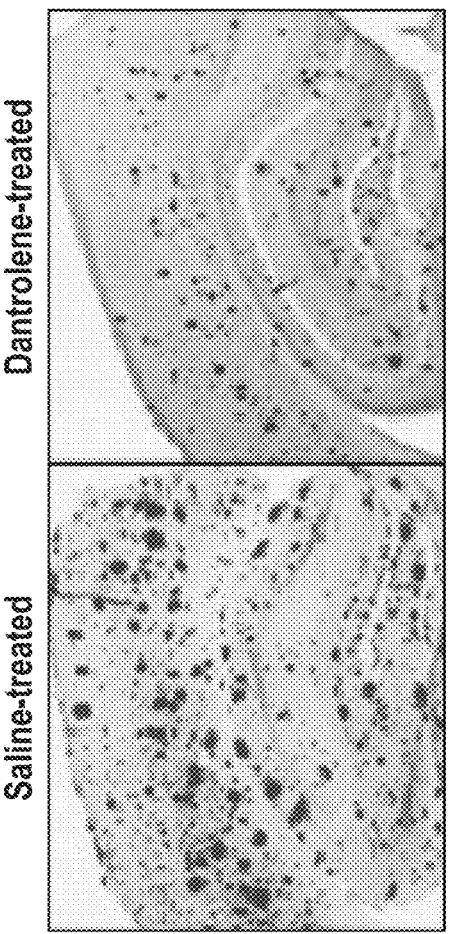

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "protein" means one or more proteins.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

When trade names are used, it is intended to independently include the trade name product formulation, the generic drug and the active pharmaceutical ingredient(s) of the trade name product.

Terms used herein may be preceded and/or followed by a single dash, "—", or a double dash, "=", to indicate the bond order of the bond between the named substituent and its parent moiety; a single dash indicates a single bond and a double dash indicates a double bond. "===" means a single or double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

When chemical structures are depicted or described, unless explicitly stated otherwise, all carbons are assumed to have hydrogen substitution to conform to a valence of four. For example, in the structure on the left-hand side of the schematic below there are nine hydrogens implied, as depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

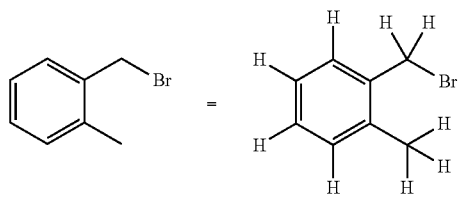

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. The term "alkylene" refers to a divalent alkyl group, where alkyl is as defined herein.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system, or a polycyclic ring system containing at least one phenyl ring. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring.

The terms "cyano" and "nitrile" as used herein, mean a —CN group.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The bicyclic heteroaryl may be attached through either cyclic moiety (e.g., either through heteroaryl or through phenyl.) Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, or purinyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle may be attached through either cyclic moiety (e.g., either through heterocycle or through phenyl.) Representative examples of heterocycle include, but are not limited to, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, 2,3-dihydrobenzofuran-2-yl, and indolinyl.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

Disclosed herein are compounds capable of normalizing neuronal calcium dyshomeostasis, of stabilizing RyR channels, and/or of normalizing aberrant neuronal calcium signaling, such as aberrant neuronal endoplasmic reticulum (ER) calcium signaling. In some embodiments, the disclosure provides methods and compositions comprising these compounds for treating neuronal or neurodegenerative disorders, such as Alzheimer's disease.

As used herein, the term "normalize" refers to returning an aberrant or abnormal biological quantity to normal or typical levels, such as levels typical of healthy neurons; alternatively, "normalize" refers to returning a state of disregulation or dyshomeostasis to a regulated state or a state of homeostasis, such as in healthy, typical, or normally functioning neurons.

As used herein, the term "calcium dyshomeostasis" refers to the disregulation of intracellular calcium in a cell, for example a neuron, for example, due to changes in the permeability of calcium channels, such as RyR channels.

The calcium ion ($Ca^{2+}$) is the main chemical messenger that helps transmit synaptic activity and depolarization status to the biochemical systems of a neuron. Thus, regulating $Ca^{2+}$ levels-maintaining "calcium homeostasis"—is a critical process in neurons, which rely on extensive and intricate $Ca^{2+}$ signaling pathways. As used herein, the term "calcium signaling" refers to all of the $Ca^{2+}$ signaling that occurs within neurons.

As used herein, the term "stabilize" when used with respect to an ion channel," such as an RyR channel, refers to modulating the flow or flux of ions through the channel, for example decreasing an abnormally high ion flux or increasing an abnormally low ion flux. In some embodiments of the methods and compositions disclosed herein, stabilizing an RyR channel with an RyR-channel stabilizing compound decreases the $Ca^{2+}$ flux through the channel, such that calcium dyshomeostasis or disregulation in a neuron is normalized and calcium homeostasis is restored.

Of particular relevance to the compositions and methods disclosed herein is the increased ER-$Ca^{2+}$ release mediated by ryanodine receptors. Ryanodine receptors (RyRs) are a class of intracellular calcium channels localized to the endoplasmic reticulum (ER) in various forms of excitable animal tissue like muscles and neurons. RyRs are activated by $Ca^{2+}$ itself in a regenerative process termed $Ca^{2+}$-induced $Ca^{2+}$ release (CICR).

In Alzheimer's disease (AD) models, the threshold for inducing CICR is significantly lowered, such that normally innocuous $Ca^{2+}$ entry triggered by synaptic stimulation or N-methyl-D-aspartate receptor (NMDAR) activation will now trigger an aberrant CICR response. Not only is the amount of RyR-$Ca^{2+}$ released abnormally high, but the cellular compartments where it occurs is abnormal, such that greatly exaggerated RyR-evoked $Ca^{2+}$ release occurs in synaptic compartments such as distal dendrites and spine heads; normally, RyR-$Ca^{2+}$ release is observed in low levels in these regions in NonTg neurons (see FIG. 1). The synaptic calcium dyshomeostasis disrupts synaptic transmission and plasticity encoding, and can drive dendritic spine loss.

Neuronal calcium dyshomeostasis is likely a central component of AD which drives early pathogenesis, and sustains amyloid pathology in sporadic AD. Furthermore, the dysregulation in synaptic calcium signals observed in the AD models is closely associated with synaptic dysfunction and structural impairment. The RyR is directly implicated in accelerating amyloid deposition (Querfurth et al., 1997, *Journal of Neurochemistry* 69:1580-1591), and in human brain studies, elevated RyRs are observed in MCI and AD patients, and are linked to cognitive decline and synaptic pathology (Kelliher et al., 1999, *Neuroscience* 92:499-513; Galeotti et al., 2008, *Learning & Memory* 15:315-323). Increased RyR2 isoform expression was also observed in human MCI patients, and in several AD mouse models (Chakroborty et al., 2009, *J. Neurosci.* 29(30):9458-70; Goussakov et al., 2010, *J Neurosci* 30:12128-12137; Bruno et al., 2012, *Neurobiology of Aging* 33:1001.e1001-1001.e106.; Antonell et al., 2013, *Neurobiology of Aging* 34:1772-1778), and others have found RyR3 upregulation at later disease stages coincident with $A\beta_{1-42}$ aggregation (Supnet et al., 2006, *Journal of Biological Chemistry* 281: 38440-38447).

In some embodiments, the methods and compositions disclosed herein comprise compounds that allosterically modulate the RyR channel, rather than non-selectively block activity as per conventional pharmacological antagonists. In this manner, the disclosed compounds normalize aberrant $Ca^{2+}$ signals and halt or prevent pathogenesis caused by calcium dyshomeostasis while leaving functional $Ca^{2+}$ signals intact.

There are multiple isoforms of ryanodine receptors: ryanodine receptor isoform 1 (RyR1) is primarily expressed in skeletal muscle; ryanodine receptor isoform 2 (RyR2) is expressed primarily in myocardium (heart muscle), but is also highly expressed in the hippocampus, as discussed below; ryanodine receptor isoform 3 (RyR3) is expressed more widely, but especially in the brain.

A particular target of interest for the methods and compositions disclosed herein is the RyR2 isoform, which is highly expressed in hippocampus, is involved in memory encoding, and is upregulated early in AD mouse models and human MCI patients. However, RyR2 is the primary cardiac isoform, and systemically 'blocking' this channel may generate undesirable off-target effects. Therefore, in some embodiments, the disclosure provides compounds with higher affinity for the RyR2 isoform compared to other isoforms.

In some embodiments, the disclosed RyR2-stabilizing compounds cause reduction in the rate of cognitive decline in early and mid-stage AD patients, along with a reduction in amyloid deposition, hyperphosphorylated tau, and a reduced conversion from MCI to AD. These effects are likely due to preservation of synaptic structure and synaptic plasticity that is compromised under conditions of sustained calcium dysregulation, such as seen during AD pathogenesis.

As the disclosed compounds are designed to stabilize RyR channel release properties through allosteric modulation of the RyR channel phosphorylation and oxidation sites, and do not serve as classical antagonists which block or reduce channel activity, there are likely no profound side effects on cardiac function (cardiac myocytes express RyR2). Rather, the compounds disclosed herein maintain normal physiological function rather than indiscriminately block calcium released from RyR channels.

In some embodiments, pharmaceutical compositions comprising the disclosed RyR-stabilizing compounds are orally available and taken daily. In some embodiments, the compounds and compositions disclosed herein are administered subcutaneously, and in some embodiments are administered every other day. In some embodiments, the compounds' effects last weeks to months. In other embodiments, the compounds' effects last over a shorter period, such as when the calcium dyshomeostasis is downstream of a pre-existing pathology. However, in other embodiments, such as when RyR-calcium dysregulation is the primary accelerant of a feed-forward pathway, the compositions and compounds disclosed herein have long-term therapeutic effects.

As the person of ordinary skill in the art will appreciate, any of the compounds disclosed herein can be provided as a derivative or prodrug, depending, e.g., on the desired end properties of the compositions and methods. For example, RyR channel stabilizers may be modified with a suitable prodrug group that metabolizes or otherwise transforms under conditions of use to yield an RyR channel stabilizer. Derivatives of RyR channel stabilizers to be used for the compositions and methods of the present disclosure are within the skill of the person skilled in the art using routine trial and experimentation.

The term "pharmaceutical formulation" refers to a preparation which is in such form as to permit the biological activity of the active ingredient to be effective, and which contains no additional components which are unacceptably toxic to a subject to which the formulation would be administered.

In some embodiments, the active ingredients of the compositions and methods disclosed herein are formulated as a pharmaceutically acceptable salt. As used herein, the term "pharmaceutically acceptable salt" includes acid and base addition salts.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

In one aspect, the disclosure provides compounds of formula (I):

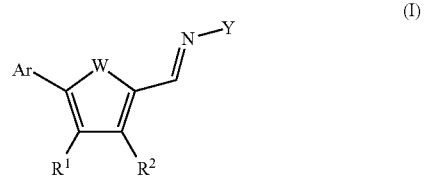

or a pharmaceutically acceptable salt thereof, wherein

Ar is aryl or heteroaryl, each of which is optionally substituted with 1, 2, 3, 4, or 5 $R^6$ groups;

W is S or O;

Y is substituted (aryl)$C_{1-6}$ alkyl- or

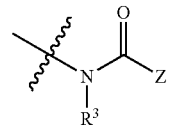

where

Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups;

$R^3$ is hydrogen, or $R^3$ together with Z optionally forms a heterocyclic ring optionally substituted with one or more of $R^7$ groups;

$R^1$ and $R^2$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$ alkylamino;

$R^4$ and $R^5$ are each independently selected from hydrogen, $C_{1-6}$ alkyl, $C_{1-6}$ haloalkyl, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and (aryl)-heteroaryl-CH=N—, or $R^4$ and $R^5$ together with nitrogen to which they are attached forms a heterocyclic ring, wherein each moiety is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino; and $R^6$ and $R^7$ are each independently selected from halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and oxo, wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino;

provided that the compound is not 1-{[5-(4-nitrophenyl)-2-furyl]methylideneamino}imidazolidine-2,4-dione or 1-{[5-(4-bromophenyl)-2-furyl]methylideneamino}imidazolidine-2,4-dione.

The disclosure also provides synthetic intermediates that are useful in making the compounds of formula II. The disclosure also provides methods of preparing compounds of the disclosure and the intermediates used in those methods.

Another aspect of the disclosure provides for pharmaceutical composition comprising a pharmaceutically acceptable carrier, solvent, adjuvant or diluent and one or more compounds of formula I.

The disclosure also provides compounds of formula I, wherein Ar is aryl optionally substituted with 1, 2, 3, 4, or 5 $R^6$ groups.

Particular embodiments based on formula I include those where Ar is phenyl optionally substituted with 1, 2, or 3 $R^6$ groups. Other embodiments provide compounds where $R^6$ is independently selected from halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, and di($C_{1-4}$ alkyl)carbamyl. For example, Ar may be phenyl, 4-chlorophenyl, 3-nitrophenyl, 2-methoxyphenyl, and 2,3-dimethyl-4-nitrophenyl.

Other particular embodiments provide for compounds where Ar is heteroaryl optionally substituted with 1, 2, 3, 4, or 5 $R^6$ groups.

Particular embodiments based on formula I include those where the compound is of formula II:

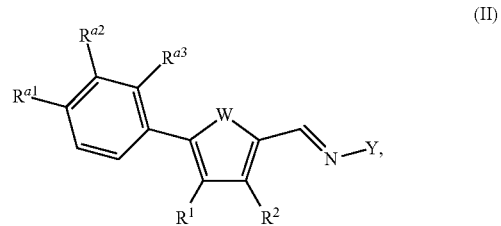

(II)

wherein $R^{a1}$, $R^{a2}$, and $R^{a3}$ are independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, and di($C_{1-4}$ alkyl)carbamyl; and $R^1$, $R^2$, W, and Y are as defined herein. Other embodiments provide for compounds of formula II where $R^{a1}$, $R^{a2}$, and $R^{a3}$ are independently selected from hydrogen, halo, nitro, hydroxy, $C_{1-6}$ alkyl, $C_{1-6}$ haloalkyl, $C_{1-6}$ alkoxy, and $C_{1-6}$ haloalkoxy. In yet another embodiment, $R^{a1}$, $R^{a2}$, and $R^{a3}$ are independently selected from hydrogen, halo, nitro, and $C_{1-6}$ alkoxy.

Particular embodiments based on formula I or II and any preceding embodiment include those where W is O.

Other particular embodiments based on formula I or II and any preceding embodiment include those where W is S.

Embodiments based on formula I or II and any preceding embodiment include those where $R^1$ and $R^2$ are each independently selected from hydrogen, $C_{1-6}$ alkyl, $C_{1-6}$ haloalkyl, $C_{1-6}$ alkoxy, $C_{1-6}$ haloalkoxy, amino, $C_{1-6}$ alkylamino, and di-$C_{1-4}$-alkylamino. Other embodiments provide for compounds of formula I or II where $R^1$ and $R^2$ are both hydrogen. In one embodiment, one of $R^1$ and $R^2$ is hydrogen are the other is $C_{1-6}$ alkyl.

Particular embodiments based on formula I or II and any preceding embodiment include those where Y is (aryl)$C_{1-6}$ alkyl-. One embodiment provides for compounds where Y is benzyl. In another embodiment, Y is 1-phenyl-ethyl-.

Particular embodiments based on formula I or II and any preceding embodiment include those where Y is

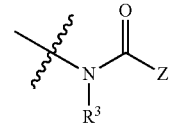

where
Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups; and $R^3$ is hydrogen.

This embodiment provides for compounds wherein Z is $C_{1-6}$ alkyl, benzyl, aryl, or heteroaryl, each optionally substituted with 1, 2, 3, 4, or 5 independently selected $R^7$ groups. For example, in one embodiment, Z may be $C_{1-6}$ alkyl, such as methyl or ethyl. In another exemplary embodiment, Z is benzyl. Other embodiments provide for compounds where Z is aryl or heteroaryl, each optionally substituted with 1, 2, 3, 4, or 5 independently selected $R^7$ groups. In one exemplary embodiment, Z is aryl optionally substituted with 1, 2, or 3 $R^7$ groups. In another exemplary embodiment, Z is phenyl optionally substituted with 1, 2, or 3 $R^7$ groups. Other embodiments provide for compounds where Z is heteroaryl optionally substituted with 1 or 2 $R^7$ groups. In one exemplary embodiment, Z is pyridinyl.

This embodiment also provides for compounds wherein Z is $NR^4R^5$.

In one embodiment, $R^4$ and $R^5$ are each independently selected from hydrogen, $C_{1-6}$ alkyl, $C_{1-6}$ haloalkyl, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and (aryl)-heteroaryl-CH=N—, wherein each optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino. Certain embodiments provide for compounds where $R^4$ and $R^5$ are hydrogen. Other embodiments provide for compounds where $R^4$ is hydrogen, and $R^5$ is $C_{1-6}$ alkyl.

In another embodiment, $R^4$ and $R^5$ together with nitrogen to which they are attached optionally forms a heterocyclic ring optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino. Other embodiments provide for compounds where $R^4$ and $R^5$ together with nitrogen form piperazinyl ring optionally substituted with $C_{1-3}$ alkyl, $C_{1-3}$ alkoxy, amino, $C_{1-3}$ alkylamino, and di-$C_{1-3}$-alkylamino.

Particular embodiments based on formula I or II and any preceding embodiment include those where Y is

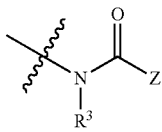

where
Z is $C_{1-6}$ alkyl, benzyl, aryl, heteroaryl, or $NR^4R^5$, wherein alkyl, benzyl, aryl, or heteroaryl is optionally substituted with 1, 2, 3, 4, or 5 independently selected $R^7$ groups; and
$R^3$ together with Z optionally forms a heterocyclic ring optionally substituted with one or more of $R^7$ groups.

This embodiment provides for compounds $R^3$ together with Z optionally forms imidazolidine-2,5-dionyl.

In some embodiments, the compound of formula (I) is selected from the compounds shown in Tables 1 and 2 or pharmaceutically acceptable salts thereof.

In another aspect, the invention provides pharmaceutical compositions comprising one or more compounds of formula (I) and a pharmaceutically acceptable carrier, excipient, or diluent. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, rectally, or via urethral, ocular intratumoral, intraventricular, intrathecal, pulmonary and irrigation method, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer or other disorder. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc. The dosage form can be designed as a sustained release or timed release.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), dextrose, mannitol, polyvinylpyrrolidone, gelatin, hydroxycellulose, acacia, suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. The liquid formulation can be buffered, isotonic solution.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 0.01% to about 99.99% by weight of one or more compounds of the invention, or a pharmaceutically acceptable salt thereof, and 99.99% to 0.01% by weight of a suitable pharmaceutical excipient. In one example, the composition will be between about 0.5% and about 75% by weight of a compound of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

In another aspect, the disclosure provides methods for normalizing neuronal calcium dyshomeostasis in a subject comprising administering to the subject one or more compounds of formula (I). In some embodiments, the subject is a human subject.

In another aspect, the disclosure provides methods for treating a neurological or neurodegenerative disorder in a subject comprising administering to the subject one or more compounds of formula (I). In some embodiments, the neurological or neurodegenerative disorder is Alzheimer's disease, Parkinson's disease, Huntington's disease, frontotemporal dementia, Pick's disease, chronic traumatic encepholopathy, traumatic brain injury, stroke, cerebellar ataxia, multiple sclerosis, Down syndrome, or an aging-related CNS disorder. In some embodiments, the neurological or neurodegenerative disorder is Alzheimer's disease. In some embodiments, the subject is a human subject.

The compounds of the invention, or their pharmaceutically acceptable salts, are administered in an "effective amount" or "therapeutically effective amount" which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 70 to about 1400 mg per day. For a normal human adult having a body weight of about 70 kilograms, a dosage in the range of about 1 to about 20 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

EXAMPLES

The Examples that follow are illustrative of specific embodiments of the invention, and various uses thereof. They are set forth for explanatory purposes only, and are not to be taken as limiting the invention.

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Example 1: Materials and Methods

Brain Slice $Ca^{2+}$ Signaling and Electrophysiology.

3×Tg-AD, TgCRND8, PS1/APP, and nontransgenic (NonTg) J29/C57BL6 control mice were bred in-house. Adult male and female mice 3-5 months old were used. Animals were cared for and used in accordance with protocols approved by the Rosalind Franklin University of Medicine and Science Animal Care and Use Committee. Hippocampal brain slices (300 μm) were prepared as previously described (Briggs et al., Neurobiol. Aging, 2013, 34:1632-1643). Mice were anesthetized with halothane, decapitated, and the brain removed into ice-cold sucrose cutting solution (200 mM sucrose, 1.5 mM KCl, 0.5 mM $CaCl_2$, 4.0 mM $MgCl_2$, 1.0 mM $KH_2PO_4$, 25 mM $NaHCO_3$, 10 mM Na-ascorbate, and 20 mM dextrose, equilibrated with 95% $O_2$/5% $CO_2$). Horizontal hippocampal slices were prepared in a Camden Instruments vibratome with the chamber filled with ice-cold sucrose cutting solution and then transferred to and maintained in standard artificial cerebrospinal fluid (aCSF; 130 mM NaCl, 2.5 mM KCl, 2.0 mM $CaCl_2$, 1.2 mM MgSO4, 1.25 mM $NaH_2PO_4$, 25 mM $NaHCO_3$, and 10 mM dextrose [305-310 mOsm], equilibrated with 95% $O_2$/5% $CO_2$, pH 7.3-7.4) at 32° C. for at least 1 hour before use. Whole-cell patch-clamp recordings were conducted at room temperature (23° C.) in continuously superfused aCSF (1.5-2.0 mL/min). Patch pipettes (5-7 MO) were filled with intracellular solution (135 mM K-gluconate, 2.0 mM $MgCl_2$, 4.0 mM $Na_2$-ATP, 0.4 mM Na-GTP, 10 mM Na-phosphocreatine, 10 mM HEPES adjusted to pH 7.3 with KOH) plus 50 μM bis-fura-2 hexapotassium (Life Technologies) as fluorescent $Ca^{2+}$ sensor. Hippocampal CA1 pyramidal neurons were identified visually via infrared differential interference contrast (IR-DIC) optics, and electrophysiologically by their passive membrane properties and spike frequency accommodation. Membrane potentials were obtained in current-clamp mode, acquired at 10 kHz with a Digidata 1322 A-D converter and Multiclamp 700B amplifier, and recorded and analyzed using pClamp 10.2 (Molecular Devices). Minianalysis 6.0.7 (Synaptosoft, Fort Lee, N.J.) was used to detect and measure spontaneous excitatory postsynaptic potential (sEPSP) events with a minimal amplitude of 0.2 mV and minimal area of 3 mV*msec. See Chakroborty et al., 2012, J. Neurosci. 32(24):8341-53 for further experimental details.

$Ca^2$ signaling was measured in individual fura-2 filled pyramidal neurons via 2-photon imaging as above, except that bath aCSF was constantly perfused and caffeine (10 mM for 1 minute) was applied through bath perfusion. Voltage-gated $Ca^{2+}$ channel (VGCC) responses were elicited by depolarization via current injected through the patch pipette with the current level adjusted to elicit a train of 8-10 spikes. VGCC $Ca^{2+}$ responses were measured 3-4 minutes prior to the caffeine RyR $Ca^{2+}$ measurement, and each slice was discarded after exposure to caffeine. Test inhibitor compounds to be assayed were introduced during a 1 hour preincubation and maintained in the aCSF perfusion before, during and after caffeine application.

Traumatic Brain Injury Induction.

Mice are deeply anesthetized with isoflurane, and have a small craniotomy performed over the sensorimotor cortex (3×3 mm) and then are given a single CCI (controlled cortical impact) with settings to produce mild TBI using the Benchmark Impactor Stereotaxic TBI device. The cortical contusion injury is administered using modified procedures developed previously (Sutton et al., 1993, J. Neurotrauma 10(2):135-49). The injury is produced by a flat and circular impactor tip (2 mm diameter). The impactor is angled 18.0 degrees away from vertical which enables the flat impactor tip to be perpendicular to the surface of the brain at the site of injury. Once in place, the impactor tip penetrates the exposed brain at 3.0 m/s at a depth of 0.6 mm below the cortical surface based on a stereotactic mouse brain atlas The injury is delivered unilaterally and the extent of cortical injury will be defined by changes in cytoarchitectural distribution following CCI. After the procedure, the scalp is sutured closed with monofilament nylon sutures using a continuous suture or an interrupted pattern and treated with lidocaine. At either 1, 7 or 30 days post TBI induction, mice are transcardially perfused, and the brains fixed with 4% paraformaldehyde. Subsequent immunostaining using standard protocols to measure phospho-tau species and amyloid species are performed in saline treated and drug treated mice.

Transcardial Perfusions.

Mice are deeply anesthetized with urethane, the thoracic cavity opened, and cannula inserted into the left ventricle of the heart, and a small hole cut into the right atrium. Ice cold saline (3 mL) and then 4% paraformaldehyde (5 mL), or 4% paraformaldehyde/1% glutaraldehyde are perfused through the circulatory system. Following this, the mice are decapitated with sharp scissors and the brain prepared for staining or microscopy.

Cell Culture and Dye Loading.

N2a cells (ATCC #CCL-131) were cultured in 50:50 Dulbecco's modified Eagle's medium: Opti-modified Eagle's medium (Gibco 11995-065:Gibco 31985-070), 5% Fetal Bovine Serum (Gibco 26140-079), 1% ABAM (Gibco 15240), and incubated at 37° C. with 10% $CO_2$. Cells were passaged using 0.05% Trypsin-EDTA (Gibco 25300-062) for 5 minutes at room temperature for non-mechanical dissociation from plate. Enzyme action was halted with 10% FBS in DMEM and cells plated onto Poly-L coated round glass slip covers (Chemglass CLS-1760-012) at 30% confluency and then grown overnight in 2.5% FBS in 50:50

DMEM:OptiMEM at 37° C. with 10% $CO_2$. The fluorescent calcium indicator, fura-2AM (Invitrogen F1201), was diluted in DMSO to 1 mM. N2a cells were incubated in 5 µM fura-2AM (diluted in fresh media) for 30 minutes, then washed in 1×PBS, fresh media was added (50:50), and allowed to de-esterify for a minimum of 15 minutes. 10 µM of dantrolene or test compound was added and incubated for 30 minutes. All incubations and washes were at 37° C. with 10% $CO_2$.

$Ca^{2+}$ Imaging and Compound Application.

Glass cover slips with fura 2-AM-filled N2a cells were placed in a submersion chamber on the stage of an upright Olympus BX51 microscope which is coupled to a 2-photon laser imaging system. To evoke a RyR-mediated calcium response, caffeine (5 mM) was bath applied via a gravity-driven perfusion system to N2a cells incubated (30 minutes) in either control media, dantrolene, or one of the test compounds (10 µM). $Ca^{2+}$ imaging of individual cells was accomplished using a custom-made video-rate 2-photon imaging system. Laser excitation was provided by 100 fs pulses at 780 nm (80 MHz) from a Ti:sapphire laser (Mai Tai Broadband, Spectra-Physics). The laser beam was scanned by a resonant galvanometer (General Scanning Lumonics), allowing rapid (7.9 kHz) bidirectional scanning in the x-axis, and by a conventional linear galvanometer in the y-axis, to provide a full-frame scan rate of 30 frames/s. The laser beam was focused onto the cells through an Olympus 40× water-immersion objective (numerical aperture 0.8). Emitted fluorescence light was detected by a wide-field photomultiplier (Electron Tubes) to derive a video signal that was captured and analyzed by Video Savant 5.0 software (10 Industries). Further analysis of background-corrected images was performed using MetaMorph software. For clarity, results are expressed as inverse ratios so that increases in [$Ca^{2+}$] correspond to increasing ratios. The % change is calculated as $[(F_0/\Delta F)-1]*100$ where $F_0$ is the average resting fluorescence at baseline and $\Delta F$ is the decrease of fluorescence reflecting $Ca^{2+}$ release. Differences between treatment groups were assessed using two-way ANOVA and Scheffe post hoc analysis for significance ($p<0.05$). Somatic $Ca^{2+}$ responses in all cells in the field of view were analyzed (n=8-20), with the nucleus region excluded. All compounds were tested in triplicate.

Example 2: RyR Stabilization by Dantrolene

The procedures set forth in Example 1 were used to investigate whether an RyR-stabilizing compound (dantrolene) is capable of affecting neuronal properties relating to AD pathogenesis and traumatic brain injury.

In two AD models (3×Tg-AD and PS1/APP), sub-chronic (4-week) treatment (5-10 mg/kg, consistent with clinical dosages in the human population) with dantrolene (1-{[5-(4-nitrophenyl)-2-furyl]methylideneamino} imidazolidine-2,4-dione; the nanocrystal formulation of dantrolene sodium is branded as RYANODEX®) returned the exaggerated ER-$Ca^{2+}$ release in dendritic spines to NonTg levels (FIG. 1), restored synaptic transmission properties and synaptic integrity (FIG. 2), significantly reduced soluble and insoluble Aβ☐ deposition (FIG. 2E), and normalized RyR2 expression (FIG. 3). Not only do these findings support a central role for RyR-$Ca^{2+}$ dysregulation in AD pathogenesis and amyloid beta aggregation, they also demonstrate that even at later disease stages therapeutic effects are obtained, which supports a feed-forward disease mechanism involving $Ca^{2+}$ dyshomeostasis, amyloid pathology, and synaptic dysfunction.

Figure 4B:
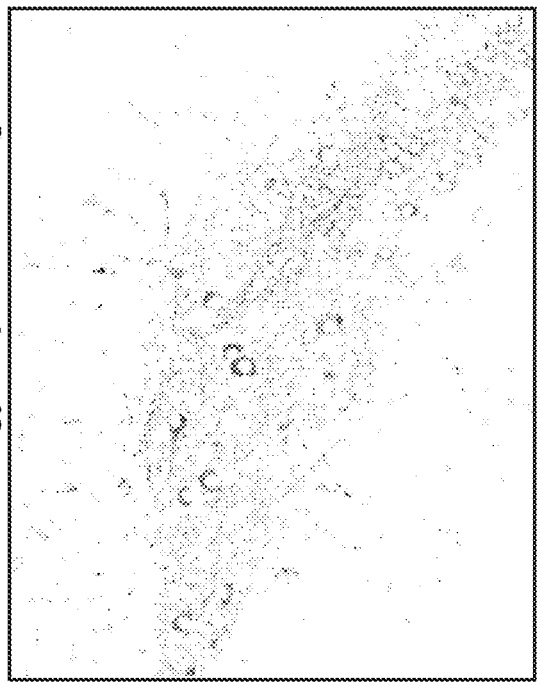
FIG. 4 shows reduction of phospho-tau levels in the hippocamus of TG-CRND8 AD mice following chronic dantrolene (Ryanodex; 10 mg/kg IP; 4 weeks) treatment. Immunostaining against phospo-tau with CP13 shows widespread staining in the dentate gyrus in saline-treated mice (4 months of age) (FIG. 4A) but not in dantrolene-treated mice (FIG. 4B). Upon stabilization of RyR-calcium signaling with dantrolene, phospho-tau staining is significantly reduced.
FIG. 4C is a histogram showing averaged % of area with CP13 fluorescence staining in the dentate gyrus. *p<0.05. n=9 slices/3 animals/group.
Figure 4A:
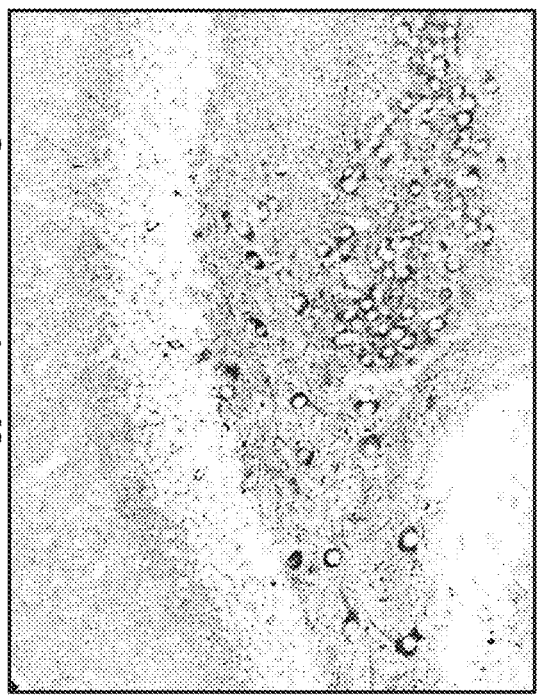
Figure 5B:
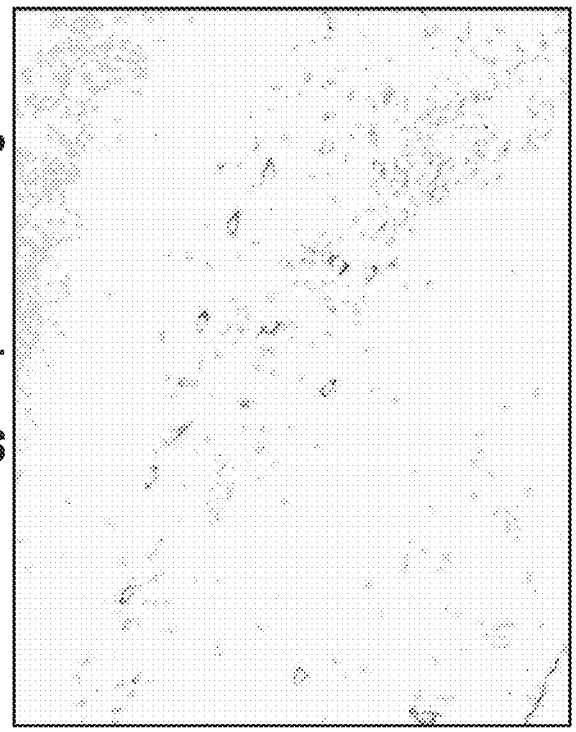
FIG. 5 shows reduction of pathological phospho-tau levels resulting from a single traumatic brain injury (controlled cortical impact) in C57 mice following chronic dantrolene (Ryanodex; 10 mg/kg IP; 4 weeks) treatment. Immunostaining against phospo-tau with CP13 shows widespread staining in the dentate gyrus in saline-treated mice (FIG. 5A) but not in dantrolene-treated mice (FIG. 5B). Upon stabilization of RyR-calcium signaling with dantrolene, CP13 phospho-tau staining is significantly reduced.
FIG. 5C is a histogram showing averaged % of area with CP13 fluorescence staining in the dentate gyrus. *p<0.05. n=6-9 slices/3 animals/group.
Figure 5A:
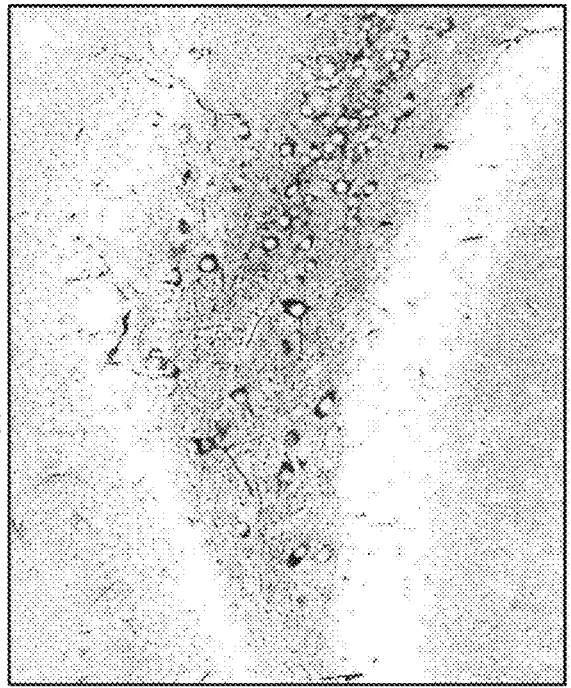

There is also evidence that stabilizing RyR function with dantrolene reduces phosphorylated tau in the TgCRND8 mouse model of AD (FIG. 4) in addition to the amyloid pathology. Similarly, in mouse models of TBI, dantrolene treatment significantly reduces the amount of phosphorylated tau staining in the hippocampal dentate gyrus (FIG. 5).

Note that chronic oral treatment (10+ months) with dantrolene has been found to increase amyloid pathology (Zhang et al., 2010, *Journal of Neuroscience* 30:8566-8580), suggesting a need for RyR2-targeting compounds that are not as pathogenic as dantrolene.

Example 3: Hit-to-Lead Optimization of RyR2-Stabilizing Compounds

Although initially based on scaffolds analogous to dantrolene,

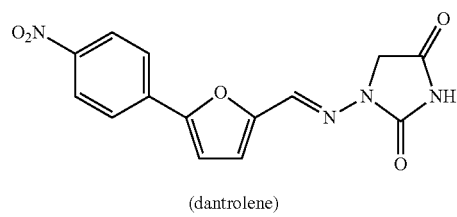 [SMILES: O=C1CN(/N=C/c2ccc(-c3ccc([N+](=O)[O-])cc3)o2)C(=O)N1]

Figure 6:
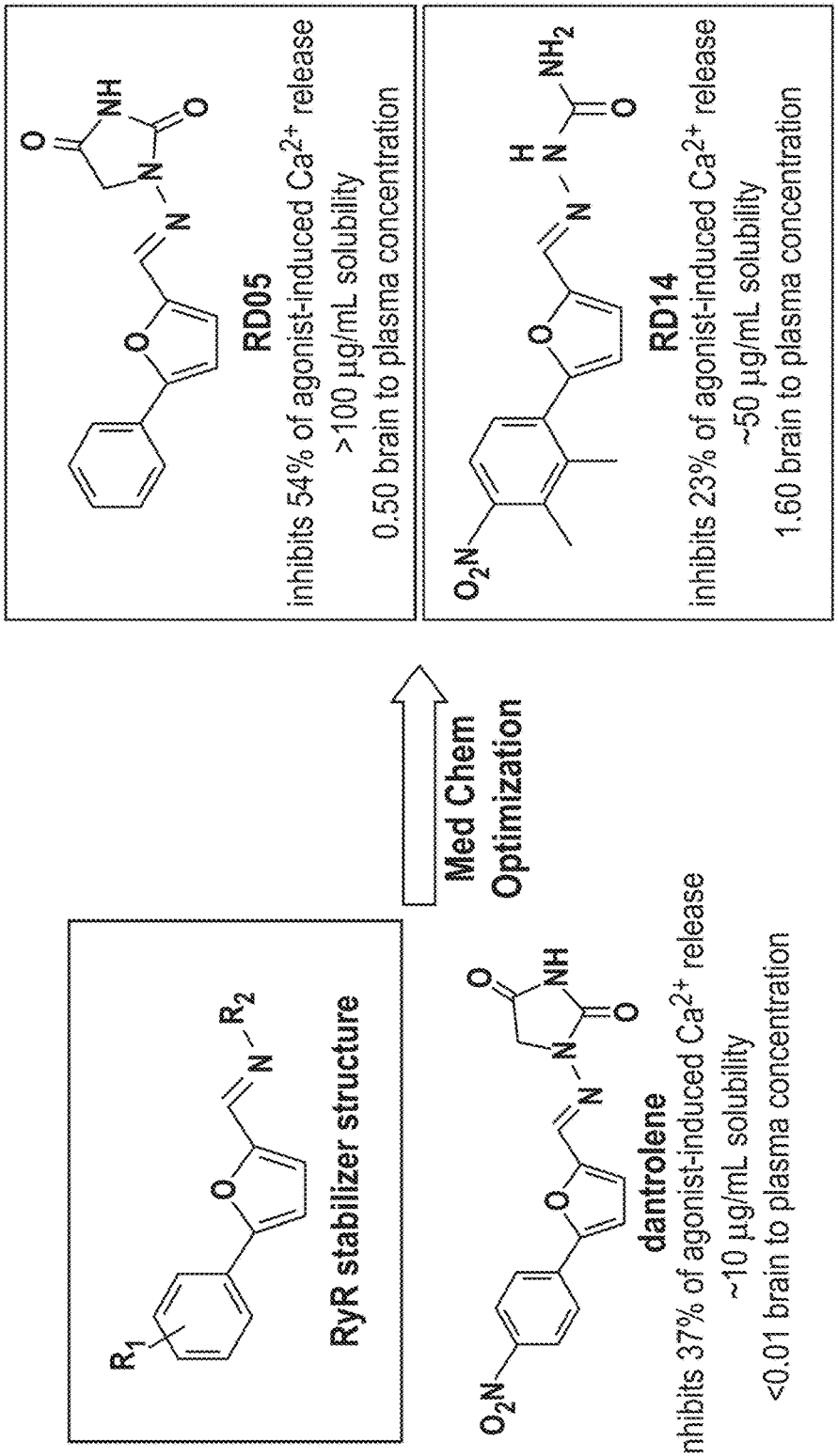
FIG. 6 shows the structures of RyR-stabilizing molecules, RD05 and RD14, which have comparable or superior effects on $Ca^{2+}$ release and markedly improved solubility and CNS penetration compared with dantrolene.

(dantrolene)

new and entirely distinct drug-like analogs have been developed that maintain robust in vitro activity and display improved drug properties (see FIG. 6). Substructural features were incorporated into dantrolene-like scaffolds to impart improved drug properties, thus enabling the development of systemically active candidates for AD and other neurodegenerative diseases.

Synthesis of the diverse RyR stabilizers was be accomplished with established Suzuki reaction chemistry followed by hydrazone formation. Twenty diverse aryl halides and 5 hydrazines were used to generate 100 new candidates. Briefly, 5-formyl-2-furylboronic acid was treated with aryl halides ($R_1$) under Suzuki reaction conditions using catalytic tetrakis(triphenylphosphine) palladium(0) in the presence of a base such as cesium carbonate. The resulting diaryl species was then subject to hydrazone formation using hydrazine derivatives ($R_2$) in 1% acetic acid/dimethylformamide. The 20 aryl halide R1 derivatives included diverse substituted benzenes and heteroaromatic aryl halides. The five R2 hydrazines included hydantoin, urea, and amide functionalities as well as different aryl groups that imparted diverse drug metabolism pharmacokinetics (DMPK) profiles.

Scheme 1

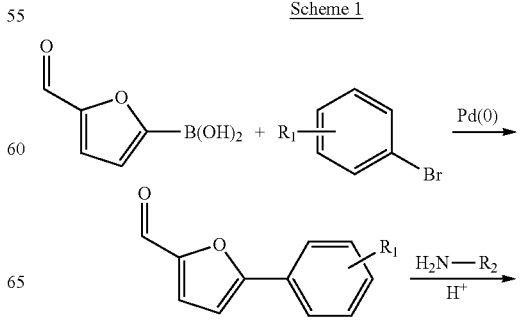

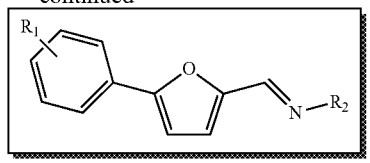

Compounds were purified and then tested by HPLC-MS and were >95% pure. Compounds exhibited aqueous solubilities ranging from 15 mg/mL to >200 mg/mL at pH 7.4. Specific emphasis was placed on the incorporation of solubilizing moieties to improve the aqueous solubility over dantrolene.

Example 4: Structure-Activity Relationships of First-Generation Compounds

Compounds were screened to determine whether they would undergo further testing or would be excluded from further investigation. The screening cascade included medicinal chemistry assays, rapid throughput screening tests in cell culture assays, acute brain slice preparations from non-transgenic (NonTg) control and AD mice, and efficacy in chronically treated AD mice. Methods for these tests are discussed in Example 1. Lead compounds were effective in N2A cells which predominantly express the RyR2 isoform.

Compounds selected after screening are identified in Table 1 and FIG. 10, which also present structure-activity relationship information for the compounds.

TABLE 1

Structure-activity relationships for compounds selected from the initial round of synthesis.

| | $R_1$ | $R_2$ | $R_3$ | $R_4$ | $R_5$ | MW | Log P | $Ca^{2+}$ Inc | Brain/ Plasma |
|---|---|---|---|---|---|---|---|---|---|
| Caffeine (+con) | — | — | — | — | | — | — | 3.09 | — |
| dantrolene | H | H | $NO_2$ | H | hydantoin | 314 | 1.7 | 1.96 | <0.01 |
| RD05 | H | H | H | H | hydantoin | 269 | 1.8 | 1.43 | 0.5 |
| RD09 | H | $NO_2$ | H | H | -NH-C(O)-CH$_3$ | 273 | 2.5 | 1.06 | nd |
| RD10 | Cl | H | $NO_2$ | H | -NH-C(O)-N-methylpiperazine | 349 | 3.4 | 4.25 | nd |
| RD11 | H | $NO_2$ | H | H | -NH-C(O)-2-pyridyl | 336 | 3.0 | 1.38 | nd |
| RD14 | $CH_3$ | $CH_3$ | $NO_2$ | H | -NH-C(O)-NH$_2$ | 302 | 3.2 | 2.38 | 1.6 |

TABLE 1-continued

Structure-activity relationships for compounds selected from the initial round of synthesis.

| | $R_1$ | $R_2$ | $R_3$ | $R_4$ | $R_5$ | MW | Log P | $Ca^{2+}$ Inc | Brain/ Plasma |
|---|---|---|---|---|---|---|---|---|---|
| RD54 | Cl | H | $NO_2$ | H | —NH—C(O)—NH—phenyl | 385 | 5.1 | >6 | nd |
| RD77 | H | H | Br | H | —NH—C(O)—(4-$NO_2$-phenyl) | 414 | 5.0 | >6 | nd |
| RD83 | H | H | $NO_2$ | H | —NH—C(O)—(2,4-diCl-phenyl) | 404 | 5.5 | >6 | nd |
| RD91 | Cl | Cl | H | H | —NH—C(O)—(2-pyridyl) | 360 | 4.4 | >6 | nd |
| RD95 | $OCH_3$ | H | H | $NO_2$ | —NH—C(O)—$NH_2$ | 304 | 2.5 | 2.11 | nd |

Several analogs effectively block RyR-evoked $Ca^{2+}$ in N2A cells when tested at 10 μM (Table 1). Dantrolene reduces caffeine's 3.09-fold $Ca^{2+}$ increase over baseline to 1.96, and also shows efficacy in the mouse model of AD. Thus, it is reasonable to conclude that analogs that show a similar or better reduction are considered active. Specifically, RD09, RD11, and RD05 block calcium release to a greater degree than dantrolene, and RD95 and RD14 are comparable to dantrolene's effect on caffeine-stimulated $Ca^{2+}$ release.

A nitro substituent on the left-hand phenyl ring appears to be important for activity as dantrolene and the most active compounds, RD09 and RD11, have this functionality. However, nitro groups are associated with reduced solubility and bioavailability. Remarkably and unexpectedly, RD05 does not possess the nitro group, yet retains all activity nonetheless. Also unexpectedly, the brain levels of RD05 are >50 times those of dantrolene. These substitutions of functional groups impart additional metabolic stability and solubility, increasing overall bioavailability compared to dantrolene.

Substitution of the hydantoin functionality of dantrolene was also explored. In several compounds, this functional group was replaced with acetyl and urea features, and the resulting compounds retained activity (for example, compounds RD09, RD95, and RD14). Aromatic features were also introduced in place of the hydantoin group of dantrolene, as in compound RD11, which add to improvements in overall DMPK as the ionizable pyridyl moiety can be transformed into various salts.

Synthetic methods for the compounds shown in Table 1 are as follows:

RD05.

5-Phenyl-2-furaldehyde (1.0 mmol) is dissolved in dimethylformamide (2 mL). This solution is added dropwise to a solution of 3-aminoimidazolidine-2,4-dione (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 270 [M+H]+. RD05 is also referred to as SM009.

RD09.

5-(3-Nitrophenyl)-2-furaldehyde (1.0 mmol) is dissolved in dimethylformamide (2 mL). This solution is added dropwise to a solution of acetic hydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 274 $[M+H]^+$.

RD10.

5-(2-Chloro-4-nitrophenyl)-2-furaldehyde (1.0 mmol) is dissolved in dimethylformamide (2 mL). This solution is added dropwise to a solution of 4-N-methyl-N-1-piperazinecarbohydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 350 $[M+H]^+$.

RD11.

5-(3-Nitrophenyl)-2-furaldehyde (1.0 mmol) is dissolved in dimethylformamide (2 mL). This solution is added dropwise to a solution of 2-pyridinecarbohydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 337 $[M+H]^+$.

RD14.

5-{4-Nitro-2,3-dimethylphenyl}-2-furaldehyde (1.0 mmol) is dissolved in dimethylformamide (2 mL). This solution is added dropwise to a solution of semicarbazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 303 $[M+H]^+$.

RD54.

5-(2-Chloro-4-nitrophenyl)-2-furaldehyde (1.0 mmol) is dissolved in dimethylformamide (2 mL). This solution is added dropwise to a solution of N-phenylhydrazinecarboxamide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 386 $[M+H]^+$.

RD77.

5-(4-Bromophenyl)-2-furaldehyde (1.0 mmol) is dissolved in dimethylformamide (2 mL). This solution is added dropwise to a solution of 4-nitrobenzhydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 415 $[M+H]^+$.

RD83.

5-(4-Nitrophenyl)-2-furaldehyde (1.0 mmol) is dissolved in dimethylformamide (2 mL). This solution is added dropwise to a solution of 2,4-dichlorobenzhydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 405 $[M+H]^+$.

RD91.

5-(2,3-Dichlorophenyl)-2-furaldehyde (1.0 mmol) is dissolved in dimethylformamide (2 mL). This solution is added dropwise to a solution of 2-pyridinecarbohydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 361 $[M+H]^+$.

RD95.

5-(2-Methoxyphenyl)-2-furaldehyde (1.0 mmol) is dissolved in dimethylformamide (2 mL). This solution is added dropwise to a solution of semicarbazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 260 $[M+H]^+$.

Example 5: Synthesis of Second-Generation Compounds

Medicinal chemistry optimization was done to provide compounds that are potent, selective, and systemically available in vivo. There have been relatively few efforts focusing on optimization of the in vivo profiles of RyR stabilizers, specifically pharmacokinetic (PK) parameters and efforts to increase brain exposure when administered systemically in vivo. Thus, second-generation synthetic efforts were focused on developing RyR stabilizers that possess an ideal ensemble of properties.

The synthetic chemistry strategy was based on the established lead series pharmacophore, exemplified by compound RD05, which exhibited significant in vitro blockage of calcium release, reasonable brain-plasma concentrations in vivo, and a potential for efficacy in our AD mouse models.

Key substructural features necessary for normalizing $Ca^{2+}$ release were identified and, using an iterative strategy, >100 analogs were synthesized that systematically interrogated each region of the pharmacophore to provide optimized candidates having an ensemble of desired physical and biological properties. Selected candidates from the optimization step, along with the lead candidates from the first-generation synthesis of compounds described in Example 3, are shown in Table 2.

TABLE 2

Selected compounds after second-generation synthesis.

| Compound | Structure |
|---|---|
| CK008 | 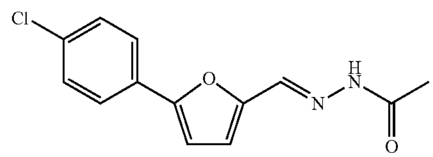 [SMILES: CC(=O)N/N=C/c1ccc(-c2ccc(Cl)cc2)o1] |
| CK010 | 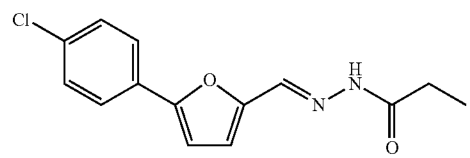 [SMILES: CCC(=O)N/N=C/c1ccc(-c2ccc(Cl)cc2)o1] |
| CK011 | 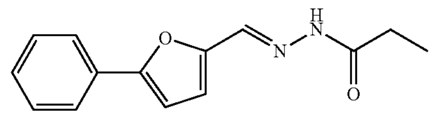 [SMILES: CCC(=O)N/N=C/c1ccc(-c2ccccc2)o1] |
| CK012 | 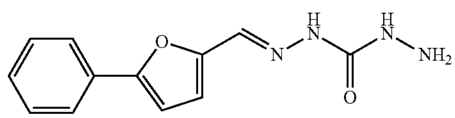 [SMILES: NNC(=O)N/N=C/c1ccc(-c2ccccc2)o1] |
| CK013 | 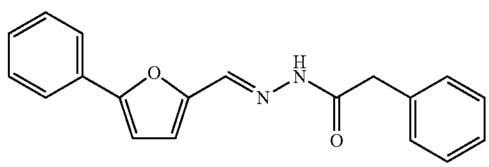 [SMILES: O=C(Cc1ccccc1)N/N=C/c1ccc(-c2ccccc2)o1] |
| CK017 | 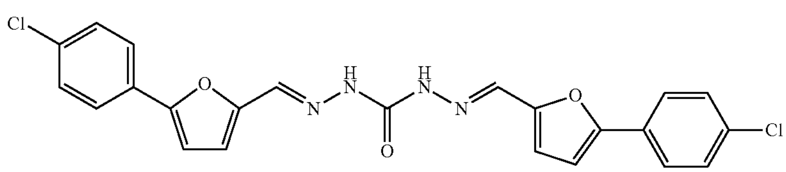 [SMILES: O=C(N/N=C/c1ccc(-c2ccc(Cl)cc2)o1)N/N=C/c1ccc(-c2ccc(Cl)cc2)o1] |
| DL041 | 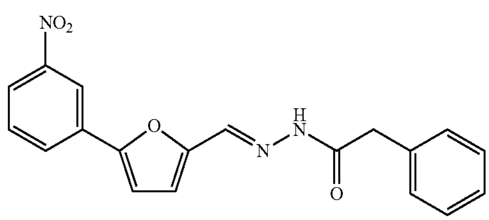 [SMILES: O=C(Cc1ccccc1)N/N=C/c1ccc(-c2cccc([N+](=O)[O-])c2)o1] |
| RD05 | 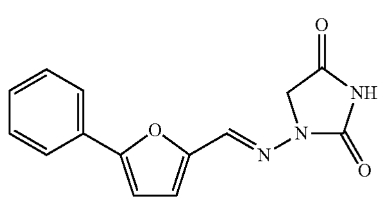 |
| RD09 | 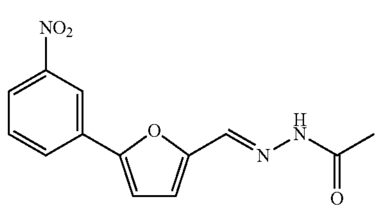 |

TABLE 2-continued

Selected compounds after second-generation synthesis.

| Compound | Structure |
|---|---|
| RD11 | 3-nitrophenyl-furan-CH=N-NH-C(O)-pyridin-2-yl |
| RD14 | 4-nitro-2,3-dimethylphenyl-furan-CH=N-NH-C(O)-NH$_2$ |
| RD95 | 2-methoxyphenyl-furan-CH=N-NH-C(O)-NH$_2$ |
| SM008 | phenyl-furan-CH=N-CH(CH$_3$)-phenyl |

Synthetic methods for the compounds shown in Table 2 (and not in Table 1) are as follows:

CK008.

5-(4-Chlorophenyl)-2-furaldehyde (1.0 mmol) is dissolved in dimethylformamide (2 mL). This solution is added dropwise to a solution of acetic hydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 263 [M+H]$^+$.

CK0010.

5-(4-Chlorophenyl)-2-furaldehyde (1.0 mmol) is dissolved in dimethylformamide (2 mL). This solution is added dropwise to a solution of propanohydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 277 [M+H]$^+$.

CK011.

N'-((5-phenylfuran-2-yl)methylene)propionohydrazide: 5-Phenyl-2-furaldehyde (50 mg, 0.29 mmol) is dissolved in dimethylformamide (1 mL). This solution is added dropwise to a solution of propionohydrazide (36.4 mg, 0.41 mmol) and 1.0 M hydrochloric acid solution in dimethylformamide (1 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford N'-((5-phenylfuran-2-yl)methylene)propionohydrazide.

CK012.

N'-((5-phenylfuran-2-yl)methylene)hydrazinecarbohydrazide: 5-Phenyl-2-furaldehyde (50 mg, 0.29 mmol) is dissolved in dimethylformamide (1 mL). This solution is added dropwise to a solution of carbohydrazide (37 mg, 0.41 mmol) and 1.0 M hydrochloric acid solution in dimethylformamide (1 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford N'-((5-phenylfuran-2-yl)methylene)hydrazinecarbohydrazide. ESI-MS: m/z 245 [M+H]$^+$.

CK013.

5-Phenyl-2-furaldehyde (1.0 mmol) is dissolved in dimethylformamide (2 mL). This solution is added dropwise to a solution of phenylacetic hydrazide (1.0 mmol) and 1.0 M hydrochloric acid solution (260 μL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 305 [M+H]$^+$.

CK017.

5-(4-Chlorophenyl)-2-furaldehyde (1.0 mmol) is dissolved in dimethylformamide (2 mL). This solution is added dropwise to a solution of carbohydrazide (0.5 mmol) and 1.0 M hydrochloric acid solution (260 µL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 468 [M+H]$^+$.

DL041.

5-(3-Nitrophenyl)-2-furaldehyde (1.0 mmol) is dissolved in dimethylformamide (2 mL). This solution is added dropwise to a solution of phenylacetic hydrazide (1.0 mmol) and 1.0 M hydrochloric acid solution (260 µL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 350 [M+H]$^+$.

SM008.

5-Phenyl-2-furaldehyde (1.0 mmol) is dissolved in dimethylformamide (2 mL). This solution is added dropwise to a solution of 1-phenylethylamine (1.0 mmol) and 1.0 M hydrochloric acid solution (260 µL) in dimethylformamide (2 mL). After addition is complete, the mixture is stirred for 25 h at rt. The mixture is diluted with water and extracted with 2 volumes of dichloromethane. The organic layers are collected and the solvent is removed by rotary evaporation. The residue is purified by preparative reverse-phase HPLC using a water-acetonitrile gradient to afford the desired product. ESI-MS: m/z 275 [M+H]$^+$.

Figure 7A:
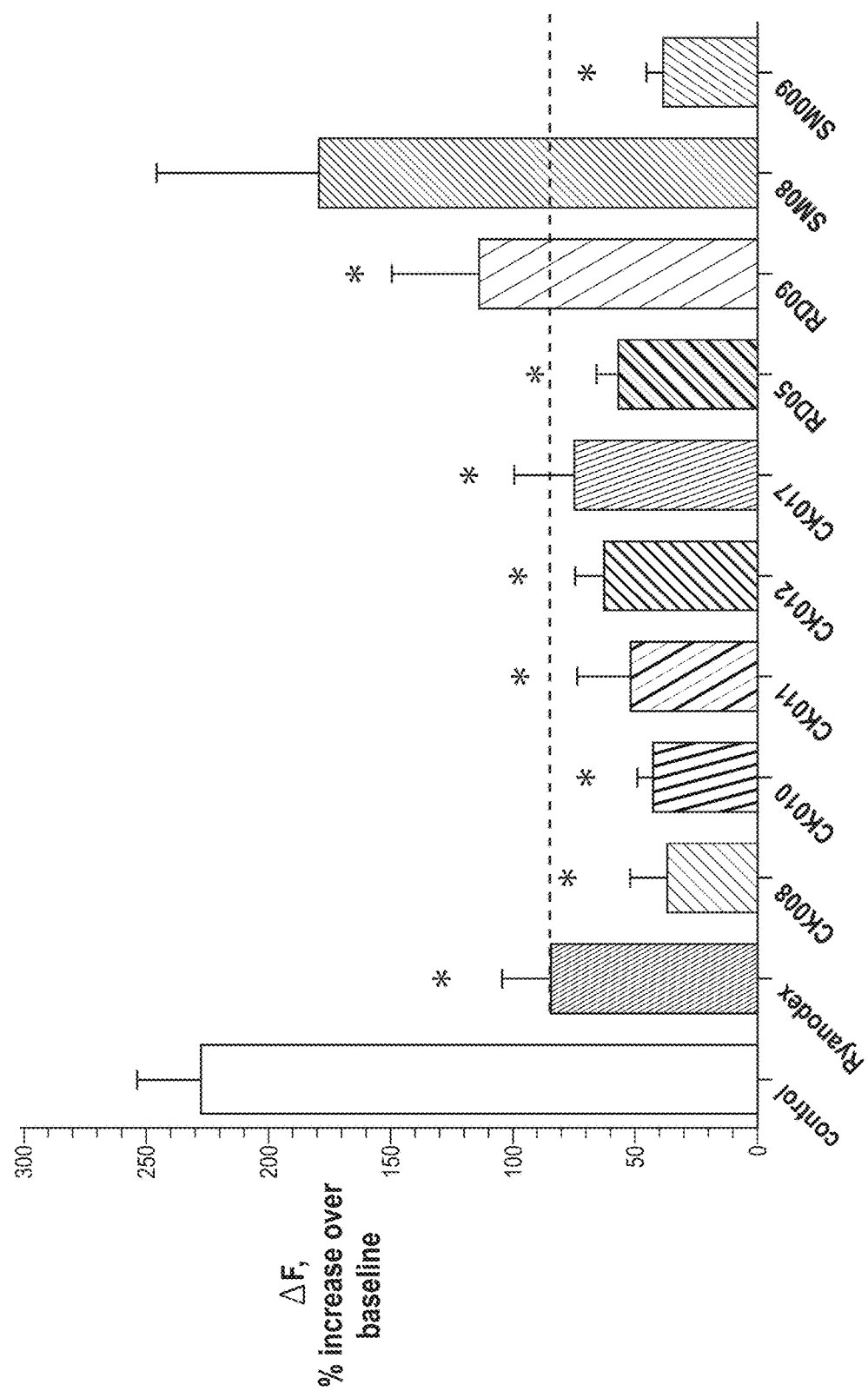

Example 6: Rapid Screening Assay in Cell Culture Systems and Neurons from AD Mice The RyR2-stabilizing compounds presented in Example 5 were tested using a RyR2-expressing N2A cell line, grown on 96 well-plates, and tested on a high speed automated imaging system as disclosed in Example 1. Compounds were screened for the ability to reduce RyR-evoked calcium in response to strong agonist stimulation, as similarly demonstrated with dantrolene (FIG. 7).

Compounds were also tested in hippocampal brain slice preparations from non-transgenic (NonTg) and AD (PS1/APP) mice as disclosed in Example 1 to determine their ability to normalize aberrant RyR-modulated calcium signals evoked by physiological stimulation in AD mice. As shown in FIG. 8A, as with dantrolene, treatment with CK013 and CK017 normalized aberrant RyR-evoked calcium signals. Treatment with all of the compounds tested had minimal effects on control NonTg mice, nor did it affect other fundamental $Ca^{2+}$ signaling events not altered in the AD mice, such as voltage-gated $Ca^{2+}$ channel influx, passive membrane properties, or spiking properties (FIGS. 8B-8D).

Example 7: In Vivo Studies

Compounds were tested with an in vivo sub-chronic treatment paradigm in NonTg and AD mice to determine if aberrant RyR-calcium responses are normalized in the AD mice while not impinging on distinct calcium pathways unaffected in AD.

Figure 9:
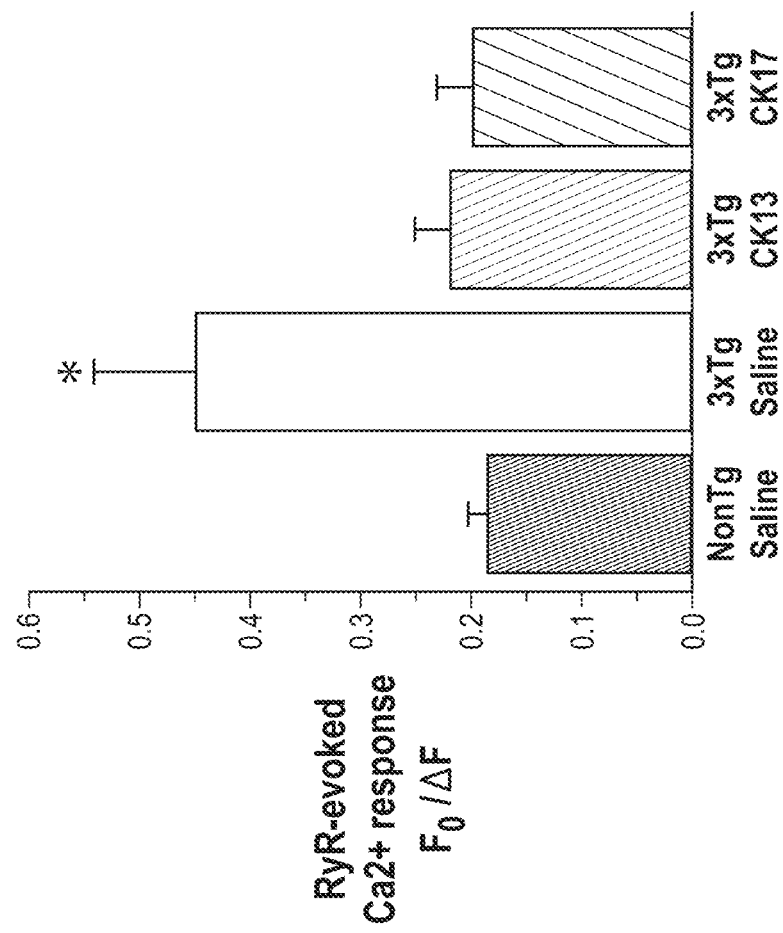
FIG. 9 shows normalization of RyR-evoked calcium responses in acute hippocampal brain slices from adult 3×Tg-AD mice following chronic treatment with RyR-channel stabilizers CK013 and CK017 (10 mg/kg, ip; 4 weeks). Peak RyR-evoked calcium responses in CA1 hippocampal neurons were evoked by bath application of 10 mM caffeine. The saline-treated 3×Tg-AD mice generated significantly larger calcium responses relative to the NonTg Saline treated mice and from the CK013 and CK017 treated 3×Tg-AD mice. Calcium responses from the CK013 and CK017 drug-treated 3×Tg-AD mice were not different from the control NonTg saline treated mice. *=One-way ANOVA: $F_{(3,38)}$=60.6; p<0.001.

$Ca^{2+}$ signaling and electrophysiological properties of CA1 pyramidal neurons were studied in hippocampal brain slices according to the protocols disclosed in Example 1. Briefly, 3xTg-AD mice were treated with either saline (0.9%), CK013 or CK017 for four weeks (10 mg/kg; ip), and then acute hippocampal brain slice preparations were made for the purposes of performing whole cell patch clamp recordings and 2-photon calcium imaging in CA1 pyramidal neurons. The objective was to determine if our compounds could restore normal RyR-mediated calcium signaling in the AD mice and maintain normal membrane physiology. The results, shown in FIG. 9, demonstrate that in both the CK013 and CK017 treated 3xTg-AD mice, the RyR-evoked calcium responses are not different from the NonTg control responses, and are significantly reduced compared to the aberrant RyR-calcium responses in the saline treated 3xTg-AD mice.

Also, passive membrane properties such as resting membrane potential and membrane input resistance were not affected by these compounds. As shown in Table 3, there were no statistically significant differences in resting membrane potential (RMP) and membrane input resistance (Ri) among the groups (p>0.05). Additionally, there were no statistically significant differences in the ratio of heart weight:body weight among the treatment groups (Table 4; p>0.05), nor were there differences in absolute body weights or heart weights among the groups (data not shown; p<0.05).

TABLE 3

Passive membrane properties from CA1 neurons.

| Strain/Treatment (n = neurons) | RMP (mV) | Ri |
|---|---|---|
| NonTg Saline (10) | −72 ± 0.1 | 154 ± 11 |
| 3xTg-AD Saline (5) | −70 ± 0.4 | 157 ± 12 |
| 3xTg-AD CK013 (15) | −69.5 ± 0.4 | 152 ± 20 |
| 3xTg-AD CK017 (14) | −69.0 ± 0.2 | 144 ± 13 |

TABLE 4

Ratio of heart weight:body weight after treatment with RyR-stabilizers.

| Strain/Treatment (n = animals) | Ratio of heart weight:body weight |
|---|---|
| NonTg Saline (4) | 4.4 × 10$^{-3}$ |
| 3xTg-AD Saline (4) | 4.05 × 10$^{-3}$ |
| 3xTg-AD CK013 (4) | 4.06 × 10$^{-3}$ |
| 3xTg-AD CK017 (4) | 3.6 × 10$^{-3}$ |

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

We claim:

1. A method for normalizing neuronal calcium dyshomeostasis in a subject in need thereof comprising administering to the subject an effective amount of the compound selected from the group consisting of:

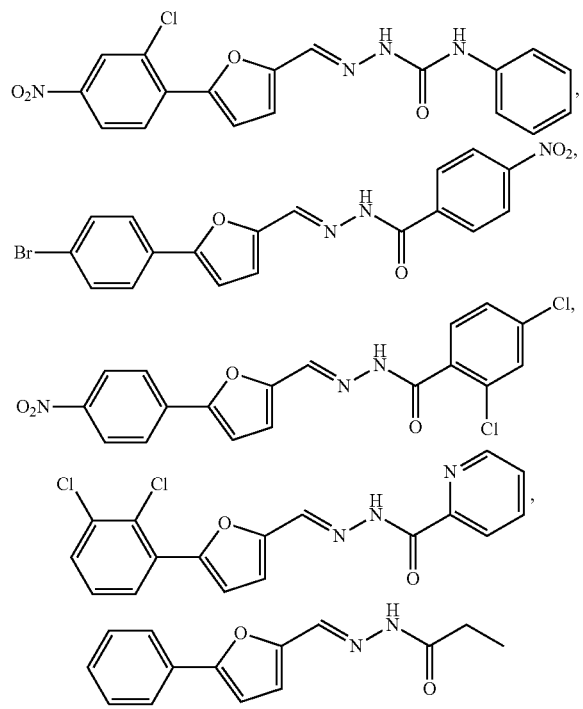

and a pharmaceutically acceptable salt thereof.

2. The method of claim 1, wherein the subject is a human subject.

3. A method for treating a neurological or neurodegenerative disorder in a subject, wherein the neurological or neurodegenerative disorder is Alzheimer's disease or traumatic brain injury, comprising administering to the subject an effective amount of the compound and a pharmaceutically acceptable salt thereof.

4. The method of claim 3 wherein the neurological or neurodegenerative disorder is traumatic brain injury.

5. The method of claim 3, wherein the neurological or neurodegenerative disorder is Alzheimer's disease.

* * * * *